(12) United States Patent
Berme et al.

(10) Patent No.: US 10,463,250 B1
(45) Date of Patent: Nov. 5, 2019

(54) SYSTEM AND METHOD FOR VISION TESTING

(71) Applicant: Bertec Corporation, Columbus, OH (US)

(72) Inventors: Necip Berme, Worthington, OH (US); Jan Jakub Ober, Columbus, OH (US)

(73) Assignee: Bertec Corporation, Columbus, OH (US)

(*) Notice: Subject to any disclaimer, the term of this patent is extended or adjusted under 35 U.S.C. 154(b) by 0 days.

(21) Appl. No.: 16/277,659

(22) Filed: Feb. 15, 2019

Related U.S. Application Data

(63) Continuation-in-part of application No. 16/022,061, filed on Jun. 28, 2018, now Pat. No. 10,264,964.
(Continued)

(51) Int. Cl.
A61B 3/14 (2006.01)
A61B 3/113 (2006.01)
(Continued)

(52) U.S. Cl.
CPC ............ *A61B 3/113* (2013.01); *A61B 3/032* (2013.01); *A61B 3/04* (2013.01); *A61B 5/163* (2017.08); *A61B 5/6803* (2013.01)

(58) Field of Classification Search
CPC ........... A61B 3/113; A61B 3/112; A61B 5/11; A61B 5/4023; A61B 5/6803; A61B 5/7257; A61B 3/0041; A61B 3/032; A61B 3/0025; A61B 3/18; A61B 5/0002; A61B 5/1121; A61B 5/163; A61B 5/4064; A61B 5/4863; A61B 5/744; A61B 3/145; A61B 5/6814; A61B 2562/0219; A61B 2562/0223; A61B 3/14; A61B 5/0071
(Continued)

(56) References Cited

U.S. PATENT DOCUMENTS 6,038,488 A 3/2000 Barnes et al.
6,113,237 A 9/2000 Ober et al.
(Continued)

OTHER PUBLICATIONS

Eye Tracker with Scene Camera, SR Research Website, Web page <http://www.sr-research.com/EL_II_scam.html>, 1 page, dated Apr. 22, 2012, retrieved from Internet Archive Wayback Machine <https://web.archive.org/web/20120422195146/http://www.sr-research.com/EL_II_scam.html> on Oct. 15, 2014.
(Continued)

Primary Examiner — Brandi N Thomas
(74) Attorney, Agent, or Firm — The Law Office of Patrick F. O'Reilly III, LLC

(57) ABSTRACT

A system for testing the vision of a subject is disclosed herein. The system includes a motion sensing device, the motion sensing device configured to measure a velocity of a head of a subject; a visual display device having an output screen, the visual display device configured to display one or more visual objects on the output screen so that the one or more visual objects are visible to the subject; and a data processing device, the data processing device operatively coupled to the motion sensing device and the visual display device, the data processing device being specially programmed to carry out the steps of the vision tests during which the subject's head undergoes an impulse displacement. A method for the testing the vision of a subject is also disclosed herein.

20 Claims, 19 Drawing Sheets

Related U.S. Application Data

(60) Provisional application No. 62/526,140, filed on Jun. 28, 2017.

(51) Int. Cl.
*A61B 3/032* (2006.01)
*A61B 5/00* (2006.01)
*A61B 5/16* (2006.01)
*A61B 3/04* (2006.01)

(58) Field of Classification Search
USPC .................. 351/208–211, 221–224, 243–246
See application file for complete search history.

(56) References Cited

U.S. PATENT DOCUMENTS

| | | |
|---|---|---|
| 6,152,564 A | 11/2000 | Ober et al. |
| 6,295,878 B1 | 10/2001 | Berme |
| 6,354,155 B1 | 3/2002 | Berme |
| 6,389,883 B1 | 5/2002 | Berme et al. |
| 6,774,885 B1 | 8/2004 | Even-Zohar |
| 6,936,016 B2 | 8/2005 | Berme et al. |
| 8,181,541 B2 | 5/2012 | Berme |
| 8,315,822 B2 | 11/2012 | Berme et al. |
| 8,315,823 B2 | 11/2012 | Berme et al. |
| D689,388 S | 9/2013 | Berme |
| D689,389 S | 9/2013 | Berme |
| 8,543,540 B1 | 9/2013 | Wilson et al. |
| 8,544,347 B1 | 10/2013 | Berme |
| 8,643,669 B1 | 2/2014 | Wilson et al. |
| 8,700,569 B1 | 4/2014 | Wilson et al. |
| 8,704,855 B1 | 4/2014 | Berme et al. |
| 8,764,532 B1 | 7/2014 | Berme |
| 8,847,989 B1 | 9/2014 | Berme et al. |
| D715,669 S | 10/2014 | Berme |
| 8,902,249 B1 | 12/2014 | Wilson et al. |
| 8,915,149 B1 | 12/2014 | Berme |
| 9,032,817 B2 | 5/2015 | Berme et al. |
| 9,043,278 B1 | 5/2015 | Wilson et al. |
| 9,066,667 B1 | 6/2015 | Berme et al. |
| 9,081,436 B1 | 7/2015 | Berme et al. |
| 9,168,420 B1 | 10/2015 | Berme et al. |
| 9,173,596 B1 | 11/2015 | Berme et al. |
| 9,200,897 B1 | 12/2015 | Wilson et al. |
| 9,277,857 B1 | 3/2016 | Berme et al. |
| D755,067 S | 5/2016 | Berme et al. |
| 9,404,823 B1 | 8/2016 | Berme et al. |
| 9,414,784 B1 | 8/2016 | Berme et al. |
| 9,468,370 B1 | 10/2016 | Shearer |
| 9,517,008 B1 | 12/2016 | Berme et al. |
| 9,526,443 B1 | 12/2016 | Berme et al. |
| 9,526,451 B1 | 12/2016 | Berme |
| 9,558,399 B1 | 1/2017 | Jeka et al. |
| 9,568,382 B1 | 2/2017 | Berme et al. |
| 9,622,686 B1 | 4/2017 | Berme et al. |
| 9,763,604 B1 | 9/2017 | Berme et al. |
| 9,770,203 B1 | 9/2017 | Berme et al. |
| 9,778,119 B2 | 10/2017 | Berme et al. |
| 9,814,430 B1 | 11/2017 | Berme et al. |
| 9,829,311 B1 | 11/2017 | Wilson et al. |
| 9,854,997 B1 | 1/2018 | Berme et al. |
| 9,916,011 B1 | 3/2018 | Berme et al. |
| 9,927,312 B1 | 3/2018 | Berme et al. |
| 10,010,248 B1 | 7/2018 | Shearer |
| 10,010,286 B1 | 7/2018 | Berme et al. |
| 10,085,676 B1 | 10/2018 | Berme et al. |
| 10,117,602 B1 | 11/2018 | Berme et al. |
| 10,126,186 B2 | 11/2018 | Berme et al. |
| 10,216,262 B1 | 2/2019 | Berme et al. |
| 2003/0216656 A1 | 11/2003 | Berme et al. |
| 2008/0228110 A1 | 9/2008 | Berme |
| 2011/0277562 A1 | 11/2011 | Berme |
| 2012/0266648 A1 | 10/2012 | Berme et al. |
| 2012/0271565 A1 | 10/2012 | Berme et al. |
| 2015/0096387 A1 | 4/2015 | Berme et al. |
| 2015/0335239 A1* | 11/2015 | Macfougall ............ A61B 3/113 351/210 |
| 2016/0080720 A1 | 3/2016 | Fullam |
| 2016/0245711 A1 | 8/2016 | Berme et al. |
| 2016/0334288 A1 | 11/2016 | Berme et al. |
| 2016/0342206 A1 | 11/2016 | Shazly et al. |
| 2018/0024015 A1 | 1/2018 | Berme et al. |

OTHER PUBLICATIONS

Eye Gaze Tracking Under Natural Head Movements, Zhiwei Zhu and Qiang Ji, 2005 IEEE.

Efficient real-time algorithms for eye state and head pose tracking in Advanced Driver Support Systems, Riad I. Hammoud, Andrew Wilhelm, Phillip Malawey, and Gerald J. Witt, 2005, IEEE.

Combined Head and Eye Tracking System for Dynamic Testing of the Vestibular System, Robert S. Allison, Moshe Eizenman, and Bob S. K. Cheung, IEEE Transactions on Biomedical Engineering, vol. 41, No. 11, Nov. 1996.

Active Eye-Tracking System by Using Quad PTZ Cameras, Chao-Ning Chan, Shunichiro Oe, Chem-Sheng Lint, IEEE 2007.

A Cascaded Scheme for Eye Tracking and Head Movement Compensation, X. Xie, R. Sudhakar, H. Zhuang, Systems and Humans, vol. 28, No. 4, Jul. 1998.

* cited by examiner

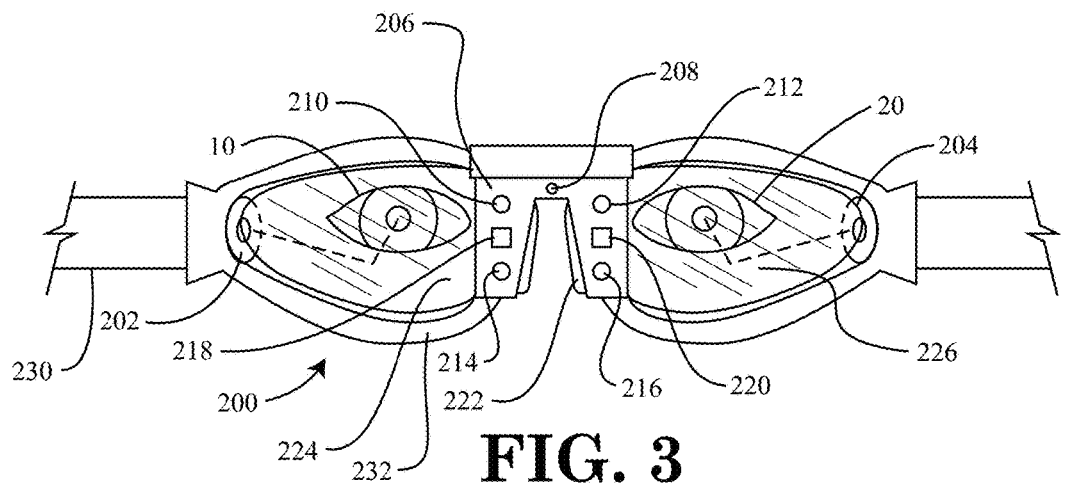
FIG. 3
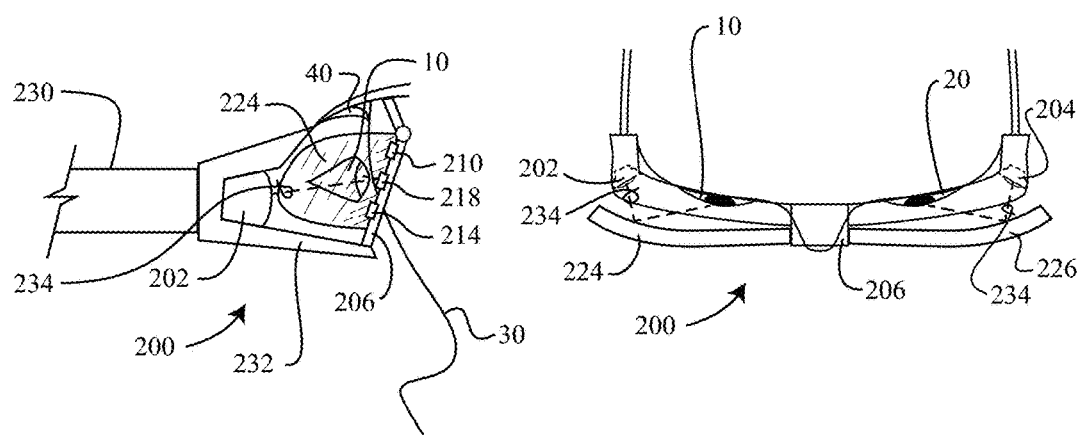
FIG. 4
FIG. 5

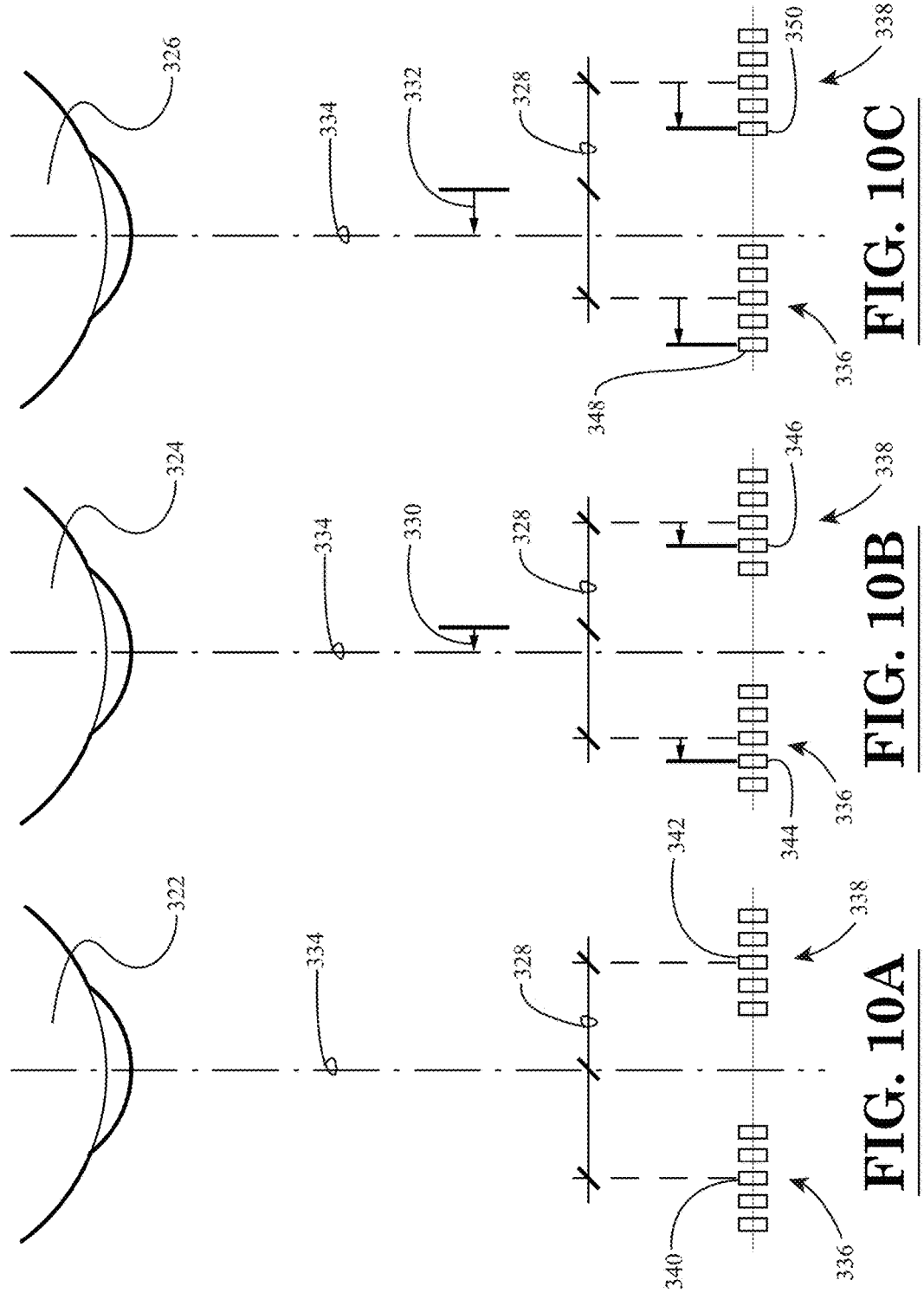

SYSTEM AND METHOD FOR VISION TESTING

CROSS-REFERENCE TO RELATED APPLICATIONS

This is a continuation-in-part of U.S. Nonprovisional patent application Ser. No. 16/022,061 entitled "Eye Movement Measurement Device", filed on Jun. 28, 2018, and further claims the benefit of U.S. Provisional Patent Application No. 62/526,140, entitled "Eye Movement Measurement Device", filed on Jun. 28, 2017, the disclosure of each of which is hereby incorporated by reference as if set forth in their entirety herein.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to a system and method for vision testing. More particularly, the invention relates to a system and method for testing the vestibulo-ocular reflex (VOR) of a subject.

2. Background

The widely used conventional method for the measurement of eye movements is the scleral search coil (SSC) method. This method involves inserting contact lenses embedded with coils on the cornea and measuring the electromagnetic signals induced in the coils.

The SSC method provides very accurate measurements of both low-speed and high-speed eye movements in three dimensions. However, the method is not suitable for routine clinical testing because of its invasiveness and because of its relatively long preparation time.

Today for clinical testing, video recording and analysis of pupil movements is the method of choice. The method is non-invasive, but high-speed cameras are exponentially more expensive. Therefore, most cameras in the video-based clinical eye movement measurement systems are limited to 250 Hz.

An alternative method is using a non-video based infrared technology that can provide much higher speeds (approximately 2,000 Hz or more). However, these systems also have limitations. For example, there is electronic drift and measuring eye movements in complete darkness is difficult and not as accurate.

What is needed, therefore, is a non-invasive eye movement measurement device that is capable of accurately measuring of both low-speed and high-speed eye movements in a clinical setting. Moreover, an eye movement measurement device is needed that enables both low-speed and high-speed eye movements to be accurately measured without requiring a long preparation time. Furthermore, a need exists for an eye movement measurement device that utilizes hybrid technology so as to minimize the limitations associated with conventional devices relying upon a single type of measurement means.

The vestibulo-ocular reflex (VOR) involves the activation of the vestibular system of a person so as to cause eye movement. More particularly, the vestibulo-ocular reflex (VOR) operates so as to stabilize images on the retina during head movement. As a result of the vestibulo-ocular reflex (VOR), a head movement in one direction will produce eye movements in the opposite direction, thus preserving the images viewed by the person on the center of the visual field. Conventional tests are known for assessing the vestibulo-ocular reflex (VOR) of subjects, but these tests have numerous limitations and drawbacks, such as not being readily customizable for particular subjects, which can affect the accuracy and reliability of these tests.

What is needed, therefore, is a system for testing the vision of a subject that implements a customizable and accurate test for testing the vestibulo-ocular reflex (VOR) of a subject. In addition, a method for testing the vision of a subject is needed that accurately tests the vestibulo-ocular reflex (VOR) of a subject by utilizing a test that is customized for the particular subject being tested.

BRIEF SUMMARY OF EMBODIMENTS OF THE INVENTION

Accordingly, the present invention is directed to a system and method for vision testing that substantially obviates one or more problems resulting from the limitations and deficiencies of the related art.

In accordance with one or more embodiments of the present invention, there is provided a system for testing the vision of a subject, which includes: a motion sensing device, the motion sensing device configured to measure a velocity of a head of a subject; a visual display device having an output screen, the visual display device configured to display one or more visual objects on the output screen so that the one or more visual objects are visible to the subject; and a data processing device, the data processing device operatively coupled to the motion sensing device and the visual display device. The data processing device is specially programmed to display one or more configurations of the one or more visual objects on the output screen of the visual display device during one or more trials of a head impulse test, the one or more configurations of the one or more visual objects being displayed after the subject's head achieves a head velocity that meets or exceeds a predetermined threshold velocity value while the subject's head undergoes an impulse displacement, the head velocity of the subject being measured by the motion sensing device, the one or more configurations of the one or more visual objects being displayed for a predetermined time period; determine whether or not the subject correctly identifies the one or more configurations of the one or more visual objects during the one or more trials of the head impulse test; generate a quantitative assessment of the subject's performance during the one or more trials of the head impulse test based upon the number of visual object configurations that the subject identified correctly during the one or more trials; and output the quantitative assessment of the head impulse test for the subject on the output screen of the visual display device.

In a further embodiment of the present invention, the one or more visual objects displayed on the output screen of the visual display device comprise one or more optotypes, the one or more optotypes comprising at least one of: (i) a Tumbling E, (ii) a Landolt C, (iii) different letters of a recognized alphabet, and (iv) any other identifiable symbol.

In yet a further embodiment, the system further comprises a user input device, the user input device configured to output an input signal in response to a manipulation of the user input device by a system user, the user input device being operatively coupled to the data processing device, the user input device configured to receive a response of the subject regarding the configuration of the one or more visual objects displayed on the output screen of the visual display device.

In still a further embodiment, the user input device is configured to accept at least four different responses of a subject, each of the at least four different responses of the subject corresponding to a different configuration of the one or more visual objects.

In yet a further embodiment, the predetermined time period during which the one or more configurations of the one or more visual objects are displayed is based upon a visual processing time determined for the subject, and wherein the data processing device is specially programmed to determine the visual processing time for the subject based upon a series of successive test trials during which a display time of the one or more visual objects is varied for the subject.

In still a further embodiment, the system further comprises an eye movement tracking device operatively coupled to the data processing device, the eye movement tracking device comprising at least one non-video-based sensor configured to detect high speed eye movements of the one or more eyes of the subject during the impulse displacement of the subject's head.

In yet a further embodiment, the data processing device is specially programmed to determine whether a correlation exists between the eye position of the subject and whether or not the subject correctly identifies the one or more configurations of the one or more visual objects.

In still a further embodiment, the data processing device is specially programmed to determine whether the subject's head achieves a preliminary threshold value prior to determining whether the subject's head velocity meets or exceeds the predetermined threshold velocity value so as to differentiate between signal noise and an impulse displacement of the subject's head; and wherein, upon determining that the subject's head achieves the preliminary threshold value, the data processing device is specially programmed to further determine whether the subject's head velocity meets or exceeds the predetermined threshold velocity value.

In yet a further embodiment, the one or more configurations of the one or more visual objects on the output screen have a display size, the display size of the one or more visual objects being determined based upon the performance of a static visual acuity test performed prior to the subject's head undergoing the impulse displacements. The data processing device is further specially programmed to, prior to the subject's head undergoes the impulse displacements, display one or more configurations of one or more visual objects having an initial size on the output screen of the visual display device while the subject maintains a generally fixed position of his or her head during the static visual acuity test; determine whether or not the subject correctly identifies the one or more configurations of the one or more visual objects having the initial size; incrementally decrease and/or increase the size of the one or more visual objects on the output screen of the visual display device during a static set of successive trials, and determine whether or not the subject correctly identifies one or more configurations of each of the differently sized visual objects during the static set of successive trials while the subject maintains a generally fixed position of his or her head; determine a size parameter of a threshold version of the one or more visual objects based upon a performance of the subject during the static set of successive trials during which the subject maintains the generally fixed position of his or her head; and set the display size of the one or more visual objects displayed while the subject's head undergoes the impulse displacements based upon the size parameter of the threshold version of the one or more visual objects.

In still a further embodiment, the motion sensing device is in the form of an inertial measurement unit.

In accordance with one or more other embodiments of the present invention, there is provided a method for testing the vision of a subject, the method comprising the steps of: (i) providing a motion sensing device, the motion sensing device configured to measure a velocity of a head of a subject; (ii) providing a visual display device having an output screen, the visual display device configured to display one or more visual objects on the output screen so that the one or more visual objects are visible to the subject; (iii) providing a data processing device, the data processing device operatively coupled to the motion sensing device and the visual display device; (iv) positioning the subject in front of the output screen of the visual display device such that one or more visual objects are visible to the subject; (v) displaying one or more configurations of the one or more visual objects on the output screen of the visual display device during one or more trials of a head impulse test, the one or more configurations of the one or more visual objects being displayed after the subject's head achieves a head velocity that meets or exceeds a predetermined threshold velocity value while the subject's head undergoes an impulse displacement, the head velocity of the subject being measured by the motion sensing device, the one or more configurations of the one or more visual objects being displayed for a predetermined time period; (vi) determining, by using the data processing device, whether or not the subject correctly identifies the one or more configurations of the one or more visual objects during the one or more trials of the head impulse test; (vii) generating, by using the data processing device, a quantitative assessment of the subject's performance during the one or more trials of the head impulse test based upon the number of visual object configurations that the subject identified correctly during the one or more trials; and (viii) outputting the quantitative assessment of the head impulse test for the subject on the output screen of the visual display device.

In a further embodiment of the present invention, the one or more visual objects displayed on the output screen of the visual display device comprise one or more optotypes, the one or more optotypes comprising at least one of: (a) a Tumbling E, (b) a Landolt C, (c) different letters of a recognized alphabet, and (d) any other identifiable symbol.

In yet a further embodiment, the method further comprises the use of a user input device, the user input device configured to output an input signal in response to a manipulation of the user input device by a system user, the user input device being operatively coupled to the data processing device; and the method further includes the step of: (ix) inputting a response of the subject regarding the configuration of the one or more visual objects into the user input device, outputting an input signal from the user input device that is indicative of the response of the subject, and transmitting the input signal of the user input device to the data processing device so that the data processing device is capable of determining whether or not the subject has correctly identified a configuration of the one or more visual objects based upon the response of the subject.

In still a further embodiment, the user input device is configured to accept at least four different responses of a subject, each of the at least four different responses of the subject corresponding to a different configuration of the one or more visual objects.

In yet a further embodiment, the predetermined time period during which the one or more configurations of the one or more visual objects are displayed is based upon a visual processing time determined for the subject; and the method further includes the step of: (ix) determining, by using the data processing device, the visual processing time for the subject based upon a series of successive test trials during which a display time of the one or more visual objects is varied for the subject.

In still a further embodiment, the method further comprises the use of an eye movement tracking device operatively coupled to the data processing device, the eye movement tracking device comprising at least one non-video-based sensor configured to detect high speed eye movements of the one or more eyes of the subject during the impulse displacement of the subject's head; and the method further includes the step of: (ix) measuring, by using the eye movement tracking device, an eye position of the subject while the subject's head undergoes the impulse displacement.

In yet a further embodiment, the method further includes the step of: (ix) determining, by using the data processing device, whether a correlation exists between the eye position of the subject and whether or not the subject correctly identifies the one or more configurations of the one or more visual objects.

In still a further embodiment, the method further includes the steps of: (ix) determining, by using the data processing device, whether the subject's head achieves a preliminary threshold value prior to determining whether the subject's head velocity meets or exceeds the predetermined threshold velocity value so as to differentiate between signal noise and an impulse displacement of the subject's head; and (x) upon determining that the subject's head achieves the preliminary threshold value, further determining, by using the data processing device, whether the subject's head velocity meets or exceeds the predetermined threshold velocity value.

In yet a further embodiment, the one or more configurations of the one or more visual objects on the output screen have a display size, the display size of the one or more visual objects being determined based upon the performance of a static visual acuity test performed prior to the subject's head undergoing the impulse displacements. The method further includes the steps of (ix) prior to the subject's head undergoing the impulse displacements, displaying one or more configurations of one or more visual objects having an initial size on the output screen of the visual display device while the subject maintains a generally fixed position of his or her head during the static visual acuity test; (x) determining, by using the data processing device, whether or not the subject correctly identifies the one or more configurations of the one or more visual objects having the initial size; (xi) incrementally decreasing and/or increasing the size of the one or more visual objects on the output screen of the visual display device using the data processing device during a static set of successive trials, and determining whether or not the subject correctly identifies one or more configurations of each of the differently sized visual objects during the static set of successive trials while the subject maintains a generally fixed position of his or her head; (xii) determining, by using the data processing device, a size parameter of a threshold version of the one or more visual objects based upon a performance of the subject during the static set of successive trials during which the subject maintains the generally fixed position of his or her head; and (xiii) setting, by using the data processing device, the display size of the one or more visual objects displayed while the subject's head undergoes the impulse displacements based upon the size parameter of the threshold version of the one or more visual objects.

In still a further embodiment, the motion sensing device is in the form of an inertial measurement unit.

It is to be understood that the foregoing summary and the following detailed description of the present invention are merely exemplary and explanatory in nature. As such, the foregoing summary and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which:

FIG. 3 is a front view of an eye movement measurement device, according to a second embodiment of the invention;

FIG. 4 is a right side view of the eye movement measurement device of FIG. 3;

FIG. 5 is a top view of the eye movement measurement device of FIG. 3;

FIG. 10A is a schematic diagram depicting an eye that is centered with respect to two sets of non-video-based sensors;

FIG. 10B is a schematic diagram depicting an eye that is displaced to the left by a first distance relative to two sets of non-video-based sensors;

FIG. 10C is a schematic diagram depicting an eye that is displaced to the left by a second distance relative to two sets of non-video-based sensors, wherein the second distance of FIG. 10C is greater than the first distance of FIG. 10B;

Throughout the figures, the same parts are always denoted using the same reference characters so that, as a general rule, they will only be described once.

DETAILED DESCRIPTION OF EMBODIMENTS OF THE INVENTION

Figure 1:
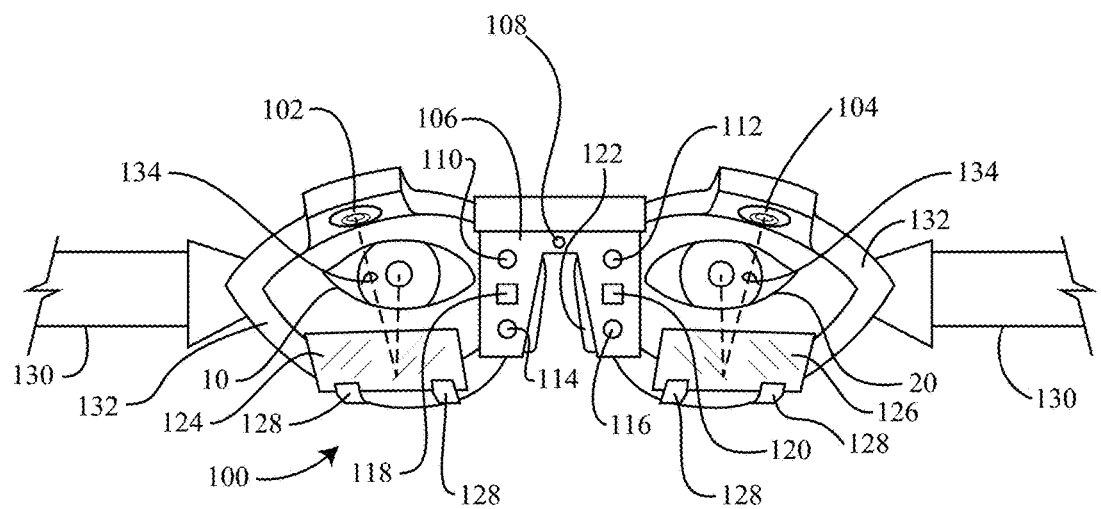
FIG. 1 is a front view of an eye movement measurement device, according to a first embodiment of the invention.
Figure 2:
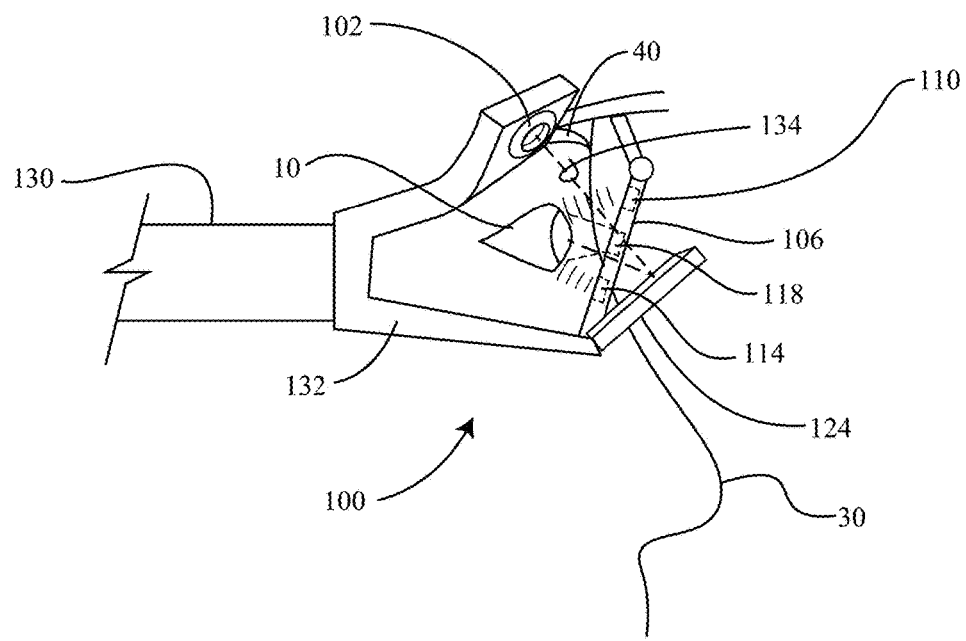
FIG. 2 is a right side view of the eye movement measurement device of FIG. 1.
Figure 7:
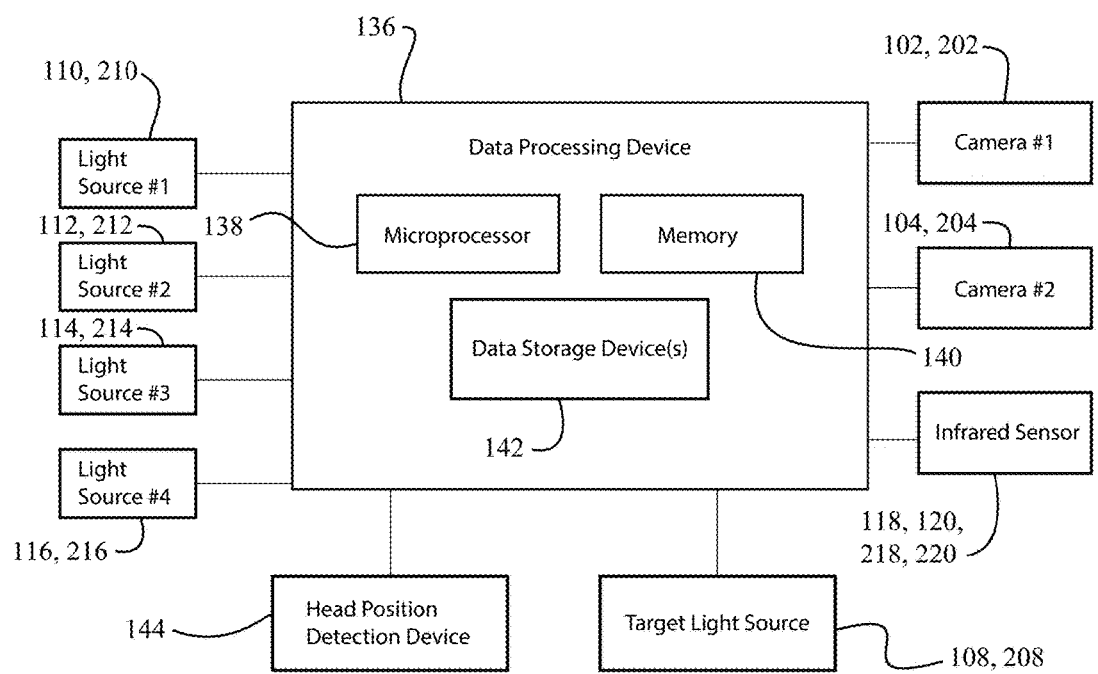
FIG. 7 is a block diagram of constituent components of the eye movement measurement devices of FIGS. 1 and 3.

A first illustrative embodiment of an eye movement measurement device is seen generally at 100 in FIGS. 1, 2, and 7. As shown in FIGS. 1, 2, and 7, the eye movement measurement device 100 of the first illustrative embodiment generally comprises a support frame 132 configured to be worn on the head of a user; a plurality of light sources 110, 112, 114, 116 mounted on the central support structure 106 of the support frame 132, the plurality of light sources 110, 112, 114, 116 configured to illuminate the eyes 10, 20 of the user; a pair of video-based sensors 102, 104 mounted on the support frame 132, the pair of video-based sensors 102, 104 configured to detect low speed eye movements of the eyes 10, 20 of the user and output a plurality of first signals based upon the detected low speed eye movements; a pair of non-video-based sensors 118, 120 mounted on the central support structure 106 of the support frame 132, the pair of non-video-based sensors 118, 120 configured to detect high speed eye movements of the one or more eyes of the user and output a plurality of second signals based upon the detected high speed eye movements; a head position detection device 144 (see FIG. 7), the head position detection device 144 configured to detect a position of the head of the user and output one or more third signals that are representative of the detected position of the head of the user; and a data processing device 136 (see FIG. 7) operatively coupled to the plurality of light sources 110, 112, 114, 116, the pair of video-based sensors 102, 104, the pair of non-video-based sensors 118, 120, and the head position detection device 144, the data processing device 136 configured to receive the plurality of first signals that are generated based upon the detected low speed eye movements, the plurality of second signals that are generated based upon the detected high speed eye movements, and the one or more third signals that are generated based upon the detected position of the head of the user, and the data processing device 136 configured to determine one or more gaze directions of the user from the plurality of first signals output by the pair of video-based sensors 102, 104, the plurality of second signals output by the pair of non-video-based sensors 118, 120, and the one or more third signals output by the head position detection device 144.

In the illustrative embodiment, the eye movement output values are given in terms of degrees of displacement. The center gaze is labeled as 0 degrees. Horizontal and vertical deviations of a line that projects out of the center of pupil from the center gaze, measured in degrees, represent the horizontal and vertical eye movements. Prior to data collection, a calibration is necessary to convert the measured parameters into actual eye movements.

In the illustrative embodiment, the calibration process involves asking the user to look back and forth among two or more pre-specified dots placed in front of the user that generate known eye angles. The values derived during the calibration process are then used to convert the measured parameters into eye movements.

Now, with reference again to FIGS. 1, 2, and 7, the plurality of light sources 110, 112, 114, 116 of the eye movement measurement device 100 will be described. As shown in the front and side views of FIGS. 1 and 2, in the illustrative embodiment, each of the plurality of light sources 110, 112, 114, 116 comprises one or more light emitting diodes (LEDs) configured to illuminate the one or more eyes of the user. The data processing device 136 is configured to activate the one or more light emitting diodes prior to detection of the low speed eye movements by the pair of video-based sensors 102, 104 and prior to detection of the high speed eye movements by the non-video-based sensors 118, 120. The light emitting diodes remain on during the entirety of the eye movement testing to illuminate the eyes of the user. In the illustrative embodiment, the plurality of light emitting diodes may be in form of infrared light emitting diodes.

Referring to FIGS. 1 and 2, the pair of video-based sensors 102, 104 of the eye movement measurement device 100 will be explained. In the illustrative embodiment, each of the pair of video-based sensors 102, 104 comprises a video camera mounted proximate to a respective eyebrow 40 of the user. In one exemplary embodiment, the pair of video cameras may comprise a pair of infrared cameras. Although, in an alternative embodiment, rather than being in the form of infrared cameras, the video cameras may be in the form of black-and-white cameras or color cameras. In the illustrative embodiment, each of the video cameras is in the form of a high-speed camera (e.g., a 250 Hz camera or other suitable high-speed camera). Also, in the illustrative embodiment, the video-based sensors 102, 104 measure low-speed eye movements, which are eye movements less than or equal to 100 degrees per second.

Next, the pair of non-video-based sensors 118, 120 will be described with reference to FIGS. 1 and 2. In the illustrative embodiment, the non-video-based sensors 118, 120 utilize direct infrared illumination and sensing means (see FIGS. 1 and 2). In the illustrative embodiment, the nasal portion of both eyes 10, 20 of the user is illuminated by infrared light and the infrared sensors 118, 120 are used to measure the amount of reflected infrared light (as shown in the diagrammatic view of FIG. 6). For example, as the corneal bulge (i.e., the protruding spherical cornea) of the eyes 10, 20 of the user moves away from the light sources 110, 112, 114, 116, less light is reflected to the infrared light detectors 118, 120, which may be in the form of photodiodes or other types of sensors for detecting infrared light. In the illustrative embodiment, the illuminators 110, 112, 114, 116 and sensors 118, 120 may be attached to the nose bridge component 122 of the head-mounted support frame 132 by means of the central support structure 106. The measurement principle of the illustrative non-video-based sensors 118, 120 is based on taking the differences between the averages of reflected light from the areas of the eyes 10, 20 near the nose 30 of the user. In the illustrative embodiment, the non-video-based sensors 118, 120 measure high-speed eye movements, which are eye movements greater than 100 degrees per second. In the illustrative embodiment, the sampling rate of the non-video-based sensors 118, 120 may be 1,000 Hz or more. In other embodiments, rather than using direct infrared illumination and sensing means for the non-video-based sensors 118, 120, the non-video-based sensors may be in the form of ultrasound sensors, electooculographic sensors, and combinations thereof.

In the illustrative embodiment, the data from the video-based sensors 102, 104 and the non-video-based sensors 118, 120 is collected in parallel. The video-based sensors 102, 104 track the centers of the pupils and convert them to eye movements. The non-video-based sensors 118, 120 track the curvature of the cornea and convert it to eye movements. Using the time stamps from both the video-based sensors 102, 104 and the non-video-based sensors 118, 120, the eye movement data from the sensors 102, 104, 118, 120 is synchronized. The measured values from the video sensors 102, 104 are used to correct for the drift of the non-video tracings. Conversely, the measured values from the non-video sensors 118, 120 are used to add samples to the tracings from the video sources. The combined tracings derived from this process can accurately represent both slow and fast eye movements.

As mentioned above, in the illustrative embodiment, the measurements from both the video-based and non-video-based sensors 102, 104, 118, 120 are eventually converted to represent eye movements in degrees. The time stamps from both sets of sensors 102, 104, 118, 120 are used to synchronize the recordings. The video-based sensors 102, 104 have a better low-frequency performance, which is used to correct for drift of the non-video-based sensors 118, 120. The non-video-based sensors 118, 120 have a better high-frequency performance, which is used to increase the number of sampling points during fast eye movements. In addition, after the data processing, eye velocities in degrees per second are eventually calculated. At the same time, the head velocities can be measured using a head position detection device 144, which may be in the form of an inertial measurement unit (IMU) embedded in the support frame 132 worn by the user. The performance of the vestibulo-ocular reflex (VOR) is quantified by comparing the head velocity versus the eye velocities. The ratio of slow eye velocities (VOR eye movements) to head velocities, as well as the number and velocity of fast eye movements (saccades) are used to quantify the subject/user performance.

Figure 6:
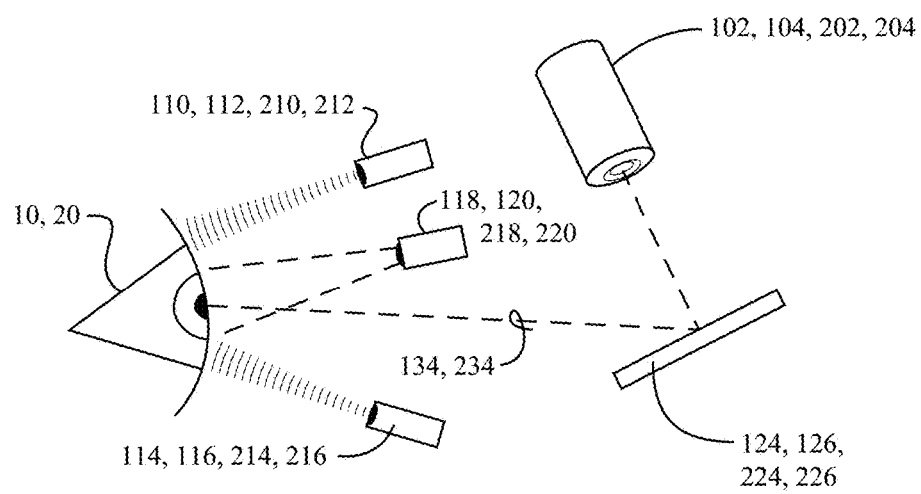
FIG. 6 is a schematic diagram illustrating the functionality of the video-based sensors and the non-video-based sensors of the eye movement measurement devices of FIGS. 1 and 3.

As shown in FIGS. 1 and 2, the eye movement measurement device 100 further includes a pair of dichroic mirrors 124, 126 mounted to the lower portion of the support frame 132. Each of the dichroic mirrors 124, 126 is secured to the lower portion of the support frame 132 by a respective pair of spaced-apart mounting brackets 128. In the first illustrative embodiment, it can be seen that the field of view of the user is substantially unobstructed by the dichroic mirrors 124, 126 because the mirrors 124, 126 are positioned below the eyes 10, 20 of the user. In the schematic diagram of FIG. 6, it can be seen each dichroic mirror 124, 126 is disposed in the path 134 of the reflected eye image between the eye 10, 20 and the respective camera 102, 104. As shown in FIG. 6, the image of the eye 10, 20 is reflected off the dichroic mirror 124, 126, and captured by the lens of the camera 102, 104.

Turning to FIG. 7, the head position detection device 144 of the eye movement measurement device 100 will be explained. In the illustrated embodiment, the head position detection device 144 is mounted on the support frame 132 that contains the pair of video-based sensors 102, 104 and the pair of non-video-based sensors 118, 120. The head position detection device 144 may be in the form of an inertial measurement unit (IMU) mounted on the support frame 132 worn by the user.

In the illustrative embodiment, it can be seen that the head-mounted support frame 132 of the eye movement measurement device 100 is in the form of an eyeglass frame worn by the user. In one or more other embodiments, the head-mounted support frame 132 may be in the form of a pair of goggles worn by the user. As shown in FIGS. 1 and 2, a head strap 130 is attached to the opposed sides of the support frame 132 for attaching the eye movement measurement device 100 to the head of the user. In the illustrative embodiment, the head strap 130 is resilient so that it is capable of being stretched to accommodate the head size of the user, and then, fitted in place on the head of the user. The head strap 130 can be formed from any suitable stretchable fabric, such as neoprene, spandex, and elastane. Alternatively, the head strap 130 could be formed from a generally non-stretchable fabric, and be provided with latching means or clasp means for allowing the head strap 130 to be split into two portions (e.g., the head strap 130 could be provided with a snap-type latching device).

In one or more further embodiments, eye movement measurement device 100 may additionally comprise a frame slippage detection device that is configured to detect a slippage of the support frame 132 relative to the head of the user. In the one or more further embodiments, the frame slippage detection device may be in the form of one or more externally disposed video cameras that are used to detect the slippage of the support frame 132. In the illustrative embodiment, the frame slippage detection device is in the form of a stationary camera disposed in front of the eye movement measurement device 100 for detecting the slippage of the support frame 132.

Also, in one or more further embodiments, the eye movement measurement device 100 may additionally comprise a light-proof cover mounted on the support frame 132. The light-proof cover is configured to at least partially surround a front of the support frame 132 so as to permit the eye movements of the user to be detected in darkness. As such, the light-proof cover enables the eye movements of the user to be recorded in complete darkness or nearly complete darkness. In one or more embodiments, the light-proof cover is in the form of a pull-down visor, such as that used on welding goggles. In one or more alternative embodiments, light-proof cover is in the form of a snap-on cover that snaps around the support frame 132, and in front of the dichroic mirrors 124, 126.

Referring again to FIG. 1, it can be seen that, in the illustrative embodiment, the eye movement measurement device 100 further comprises a target generation device (e.g., a target light source 108) mounted on the support frame 132. The target generation device 108 is configured to generate a target and project the target onto a surface (e.g., a wall surface) in front of the user such that the target is visible by the eyes 10, 20 of the user. The target generation device 108 may be in the form of a laser light source or a light emitting diode.

In addition, in one or more embodiments, the eye movement measurement device 100 further comprises a data storage device mounted on the support frame 132. The data storage device comprises non-volatile data storage means, and is configured to store eye movement data so as to enable the eye movement data to be subsequently downloaded to a remote computing device.

Now, turning to FIG. 7, it can be seen that the illustrated data acquisition/data processing device 136 (e.g., a computing device) of the eye movement measurement device 100 includes a microprocessor 138 for processing data, memory 140 (e.g., random access memory or RAM) for storing data during the processing thereof, and data storage device(s) 142, such as one or more hard drives, compact disk drives, floppy disk drives, flash drives, or any combination thereof. As shown in FIG. 7, the light sources 110, 112, 114, 116, the pair of video-based sensors 102, 104, and the pair of non-video-based sensors 118, 120 are operatively coupled to the data acquisition/data processing device 136. Also, as illustrated in FIG. 7, the target light source 108 and the head position detection device 144 are operatively coupled to the data acquisition/data processing device 136. In some embodiments, the data acquisition/data processing device 136 can be in the form of a desktop computer or laptop computer remotely located from the support frame 132 of the eye movement measurement device 100, while in other embodiments, the data acquisition/data processing device 136 can be embodied as a mini-computer mounted on the support frame 132.

In the illustrative embodiment, the data processing device 136 is operatively coupled to the light sources 110, 112, 114, 116, the pair of video-based sensors 102, 104, the pair of non-video-based sensors 118, 120, the target light source 108 and the head position detection device 144 by means of a wireless connection. In an alternative embodiment, the data processing device 136 may be operatively coupled to the light sources 110, 112, 114, 116, the pair of video-based sensors 102, 104, the pair of non-video-based sensors 118, 120, the target light source 108 and the head position detection device 144 by means of a hardwired connection.

FIGS. 3-5 illustrate an eye movement measurement device 200 according to a second illustrative embodiment of the present invention. With reference to these figures, it can be seen that, in many respects, the second illustrative embodiment is similar to that of the first embodiment. Moreover, some parts are common to both such embodiments. For the sake of brevity, the elements that the second embodiment of the eye movement measurement device has in common with the first embodiment will only be briefly mentioned, if at all, because these components have already been explained in detail above Initially, referring collectively to FIGS. 3-5 and 7, it can be seen that, like the first illustrative embodiment, the eye movement measurement device 200 of the second illustrative embodiment generally comprises a support frame 232 configured to be worn on the head of a user; a plurality of light sources 210, 212, 214, 216 mounted on the central support structure 206 of the support frame 232, the plurality of light sources 210, 212, 214, 216 configured to illuminate the eyes 10, 20 of the user; a pair of video-based sensors 202, 204 mounted on the support frame 232, the pair of video-based sensors 202, 204 configured to detect low speed eye movements of the eyes 10, 20 of the user and output a plurality of first signals based upon the detected low speed eye movements; a pair of non-video-based sensors 218, 220 mounted on the central support structure 206 of the support frame 232, the pair of non-video-based sensors 218, 220 configured to detect high speed eye movements of the one or more eyes of the user and output a plurality of second signals based upon the detected high speed eye movements; a head position detection device 144 (see FIG. 7), the head position detection device 144 configured to detect a position of the head of the user and output one or more third signals that are representative of the detected position of the head of the user; and a data processing device 136 (see FIG. 7) operatively coupled to the plurality of light sources 210, 212, 214, 216, the pair of video-based sensors 202, 204, the pair of non-video-based sensors 218, 220, and the head position detection device 144, the data processing device 136 configured to receive the plurality of first signals that are generated based upon the detected low speed eye movements, the plurality of second signals that are generated based upon the detected high speed eye movements, and the one or more third signals that are generated based upon the detected position of the head of the user, and the data processing device 136 configured to determine one or more gaze directions of the user from the plurality of first signals output by the pair of video-based sensors 202, 204, the plurality of second signals output by the pair of non-video-based sensors 218, 220, and the one or more third signals output by the head position detection device 144.

As explained above for the first illustrative embodiment, the eye movement output values are given in terms of degrees of displacement. The center gaze is labeled as 0 degrees. Horizontal and vertical deviations of a line that projects out of the center of pupil from the center gaze, measured in degrees, represent the horizontal and vertical eye movements.

Now, with reference again to FIGS. 3-5 and 7, the plurality of light sources 210, 212, 214, 216 of the eye movement measurement device 200 will be described. As shown in the front and side views of FIGS. 3 and 4, in the illustrative embodiment, each of the plurality of light sources 210, 212, 214, 216 comprises one or more light emitting diodes (LEDs) configured to illuminate the one or more eyes of the user. The data processing device 136 is configured to activate the one or more light emitting diodes prior to detection of the low speed eye movements by the pair of video-based sensors 202, 204 and prior to detection of the high speed eye movements by the non-video-based sensors 218, 220. The light emitting diodes remain on during the entirety of the eye movement testing to illuminate the eyes of the user. As described above for the first embodiment, in the illustrative embodiment, the plurality of light emitting diodes may be in form of infrared light emitting diodes.

Referring to FIGS. 3 and 4, the pair of video-based sensors 202, 204 of the eye movement measurement device 200 will be explained. In the illustrative embodiment, each of the pair of video-based sensors 202, 204 comprises a video camera mounted proximate to a respective temple of the user (i.e., each video camera 202, 204 is disposed outwardly from a respective eye of the user—see FIG. 3). In one exemplary embodiment, the pair of video cameras may comprise a pair of infrared cameras. Although, in an alternative embodiment, rather than being in the form of infrared cameras, the video cameras may be in the form of black-and-white cameras or color cameras. In the illustrative embodiment, each of the video cameras is in the form of a high-speed camera (e.g., a 250 Hz camera or other suitable high-speed camera). Also, in the illustrative embodiment, the video-based sensors 202, 204 measure low-speed eye movements, which are eye movements less than or equal to 100 degrees per second.

Next, the pair of non-video-based sensors 218, 220 will be described with reference to FIGS. 3 and 4. In the illustrative embodiment, the non-video-based sensors 218, 220 utilize direct infrared illumination and sensing means (see FIGS. 3 and 4). In the illustrative embodiment, the nasal portion of both eyes 10, 20 of the user is illuminated by infrared light and the infrared sensors 218, 220 are used to measure the amount of reflected infrared light (as shown in the diagrammatic view of FIG. 6). For example, as the corneal bulge (i.e., the protruding spherical cornea) of the eyes 10, 20 of the user moves away from the light sources 210, 212, 214, 216, less light is reflected to the infrared light detectors 218, 220, which may be in the form of photodiodes or other types of sensors for detecting infrared light. In the illustrative embodiment, the illuminators 210, 212, 214, 216 and sensors 218, 220 may be attached to the nose bridge component 222 of the head-mounted support frame 232 by means of the central support structure 206. The measurement principle of the illustrative non-video-based sensors 218, 220 is based on taking the differences between the averages of reflected light from the areas of the eyes 10, 20 near the nose 30 of the user. In the illustrative embodiment, the non-video-based sensors 218, 220 measure high-speed eye movements, which are eye movements greater than 100 degrees per second. In other embodiments, rather than using direct infrared illumination and sensing means for the non-video-based sensors 218, 220, the non-video-based sensors may be in the form of ultrasound sensors, electooculographic sensors, and combinations thereof.

As described above for the first illustrative embodiment, the data from the video-based sensors 202, 204 and the non-video-based sensors 218, 220 is collected in parallel. The video-based sensors 202, 204 track the centers of the pupils and convert them to eye movements. The non-video-based sensors 218, 220 track the curvature of the cornea and convert it to eye movements. Using the time stamps from both the video-based sensors 202, 204 and the non-video-based sensors 218, 220, the eye movement data from the sensors 202, 204, 218, 220 is synchronized. The measured values from the video sensors 202, 204 are used to correct for the drift of the non-video tracings. Conversely, the measured values from the non-video sensors 218, 220 are used to add samples to the tracings from the video sources. The combined tracings derived from this process can accurately represent both slow and fast eye movements.

As mentioned above, in the illustrative embodiment, the measurements from both the video-based and non-video-based sensors 202, 204, 218, 220 are eventually converted to represent eye movements in degrees. The time stamps from both sets of sensors 202, 204, 218, 220 are used to synchronize the recordings. The video-based sensors 202, 204 have a better low-frequency performance, which is used to correct for drift of the non-video-based sensors 218, 220. That is, the output data from the video-based sensors 202, 204 may be used to determine the amount by which the sampling curve produced by the non-video-based sensors 218, 220 is shifted or offset due to the effects of sensor drift. The non-video-based sensors 218, 220 have a better high-frequency performance, which is used to increase the number of sampling points during fast eye movements. That is, the additional sampling points generated by the non-video-based sensors 218, 220 may be used to fill-in sampling points between the sampling points generated using the video-based sensors 202, 204 by using an interpolation algorithm, etc. (e.g., a quadratic interpolation algorithm). For example, the equation provided below may be used to align the curves generated by the video-based sensors 202, 204 and the non-video-based sensors 218, 220 so that the drift and additional sampling point corrections may be applied:

$$\vec{N} = a \cdot I \cdot \vec{S} + b \quad (1)$$

where:

$\vec{N}$: interpolated values for a series of time points obtained from the video-based sensor(s);

I: identity matrix; and $\vec{S}$: sensed values for the same time points obtained from the non-video-based sensors. In addition to applying the drift and additional sampling point corrections, in the illustrative embodiment, a cross-correlation technique may also be applied so as to correct for an unknown time shift due to an unknown latency in the video output data generated by the video-based sensors 202, 204 (i.e., cameras). In addition, after the data processing, eye velocities in degrees per second are eventually calculated. At the same time, the head velocities can be measured using the head position detection device 144, which may be in the form of an inertial measurement unit (IMU) embedded in the support frame 232 worn by the user. The performance of the vestibulo-ocular reflex (VOR) is quantified by comparing the head velocity versus the eye velocities. The ratio of slow eye velocities (VOR eye movements) to head velocities, as well as the number and velocity of fast eye movements (saccades) are used to quantify the subject/user performance.

As shown in FIGS. 3-5, the eye movement measurement device 200 further includes a pair of dichroic mirrors 224, 226 mounted to the central support structure 206 of the support frame 232. In the second illustrative embodiment, it can be seen that the dichroic mirrors 224, 226 are disposed in front of the eyes 10, 20 of the user so as to generally cover the field of view of the user, rather than being positioned below the eyes 10, 20 of the user, as in the first illustrative embodiment. Each of the dichroic mirrors 224, 226 is configured so as to reflect the eye image back to the camera 202, 204, yet still allow the user to see through the mirror 224, 226 so that the surrounding environment is visible to him or her. Particularly, in the schematic diagram of FIG. 6, it can be seen each dichroic mirror 224, 226 is disposed in the path 234 of the reflected eye image between the eye 10, 20 and the respective camera 202, 204. As shown in FIG. 6, the image of the eye 10, 20 is reflected off the dichroic mirror 224, 226, and captured by the lens of the camera 202, 204.

Turning to FIG. 7, the head position detection device 144 of the eye movement measurement device 200 will be explained. Similar to that described above for the first illustrative embodiment, the head position detection device 144 is mounted on the support frame 232 that contains the pair of video-based sensors 202, 204 and the pair of non-video-based sensors 218, 220. The head position detection device 144 may be in the form of an inertial measurement unit (IMU) mounted on the support frame 232 worn by the user.

In the illustrative embodiment, it can be seen that the head-mounted support frame 232 of the eye movement measurement device 200 is in the form of an eyeglass frame worn by the user. In one or more other embodiments, the head-mounted support frame 232 may be in the form of a pair of goggles worn by the user. As shown in FIGS. 3 and 4, a head strap 230 is attached to the opposed sides of the support frame 232 for attaching the eye movement measurement device 200 to the head of the user. In the illustrative embodiment, the head strap 230 is resilient so that it is capable of being stretched to accommodate the head size of the user, and then, fitted in place on the head of the user. The head strap 230 can be formed from any suitable stretchable fabric, such as neoprene, spandex, and elastane. Alternatively, the head strap 230 could be formed from a generally non-stretchable fabric, and be provided with latching means or clasp means for allowing the head strap 230 to be split into two portions (e.g., the head strap 230 could be provided with a snap-type latching device).

In one or more further embodiments, eye movement measurement device 200 may additionally comprise a frame slippage detection device that is configured to detect a slippage of the support frame 232 relative to the head of the user. In the one or more further embodiments, the frame slippage detection device may be in the form of one or more externally disposed video cameras that are used to detect the slippage of the support frame 232. In the illustrative embodiment, the frame slippage detection device is in the form of a stationary camera disposed in front of the eye movement measurement device 200 for detecting the slippage of the support frame 232.

Also, in one or more further embodiments, the eye movement measurement device 200 may additionally comprise a light-proof cover mounted on the support frame 232. The light-proof cover is configured to at least partially surround a front of the support frame 232 so as to permit the eye movements of the user to be detected in darkness. As such, the light-proof cover enables the eye movements of the user to be recorded in complete darkness or nearly complete darkness. In one or more embodiments, the light-proof cover is in the form of a pull-down visor, such as that used on welding goggles. In one or more alternative embodiments, light-proof cover is in the form of a snap-on cover that snaps around the support frame 232, and in front of the dichroic mirrors 224, 226.

Figure 8:
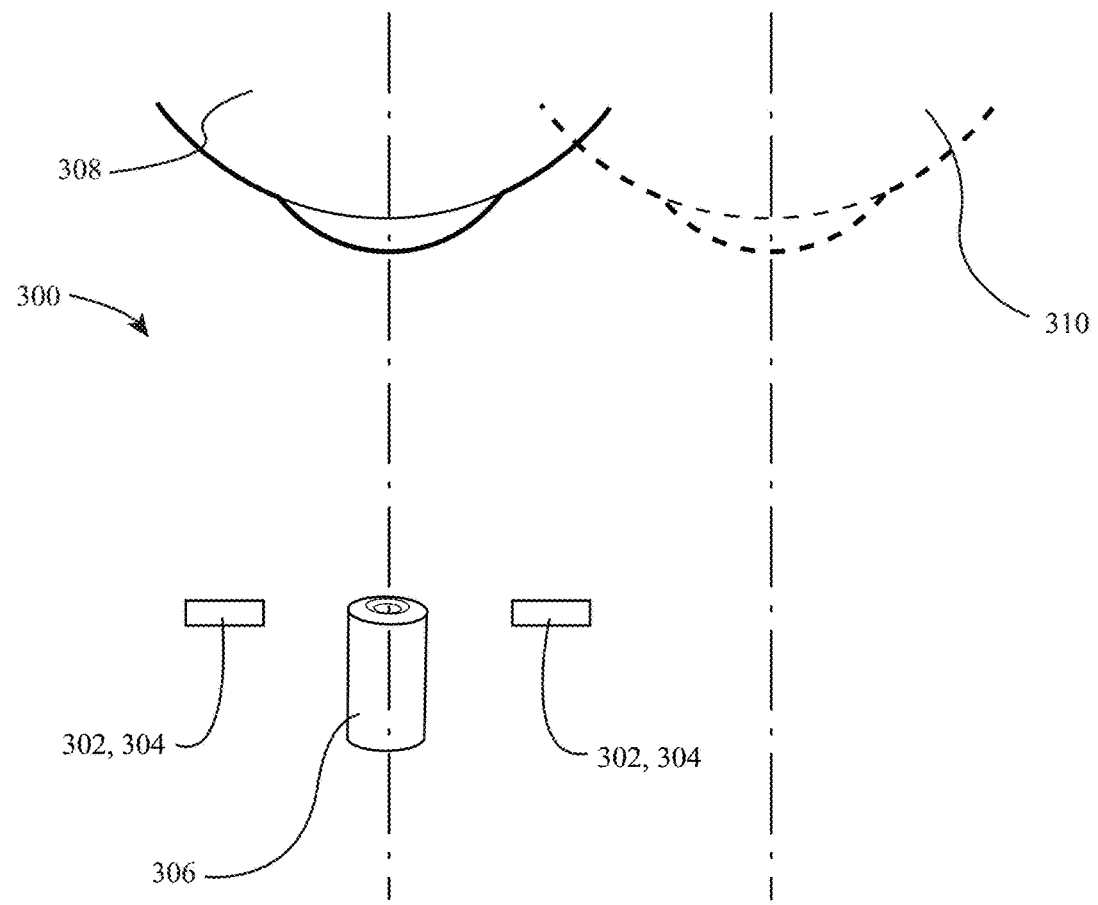
FIG. 8 is a schematic diagram illustrating the manner in which a video-based sensor is capable of being used for the alignment of non-video-based sensors.
Figure 9:
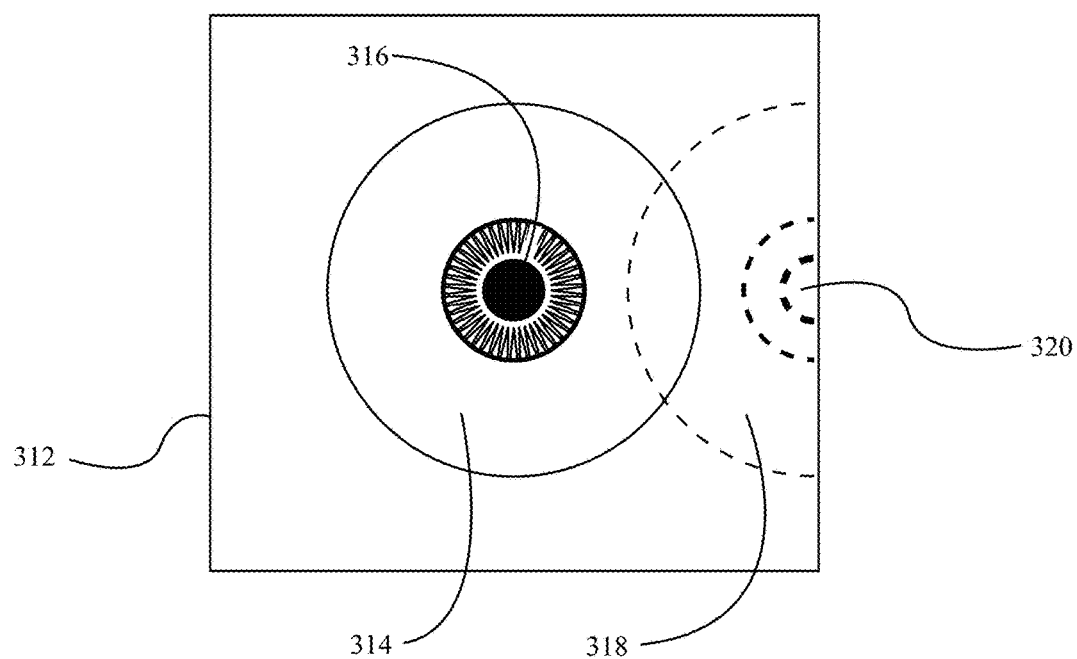
FIG. 9 depicts an example alignment of an eye using an image captured by the video-based sensor of FIG. 8.

In addition, in one or more further embodiments, the non-video-based sensors (e.g., infrared sensors) may be located relative to the optical of axis of the video-based sensor(s) (e.g., a camera) according to a known relationship (e.g., a predetermined distance or distances between the sensors, etc.) so as to enable the video-based sensor(s) to be used for the alignment of the non-video-based sensors. For example, as shown in the schematic diagram 300 of FIG. 8, non-video-based sensors 302, 304 are arranged on opposite sides of the video-based sensor 306, which may be in the form of a camera 306. More specifically, the non-video-based sensors 302, 304 are spaced apart from the camera optical axis (as indicated by the centerline in FIG. 8) by known horizontal distances. In FIG. 8, the actual position of the eye 310 is shown offset to the right of the optical axis of the camera 306. As shown in FIG. 8, the desired position of the eye 308 is centered on the camera optical axis. Because a known fixed relationship exists between the location of the camera 306 and the non-video-based sensors 302, 304 in FIG. 8, the non-video-based sensors 302, 304 may be aligned in accordance with the actual position of the eye 310 by using the image information obtained from the camera 306. For example, FIG. 9 depicts an example alignment of an eye using an image 312 captured by the camera 306 in FIG. 8. In FIG. 9, the eye 318 with pupil 320 depicts the actual location of the eye as captured by the camera 306, while the centered eye 314 with pupil 316 depicts the desired position of the eye in the image. The offset distance between the eye 318 and the eye 314 in FIG. 9 may be used to adjust the non-video-based sensors 302, 304 of FIG. 8 to account for the non-centered position of the eye 318.

Figure 11A:
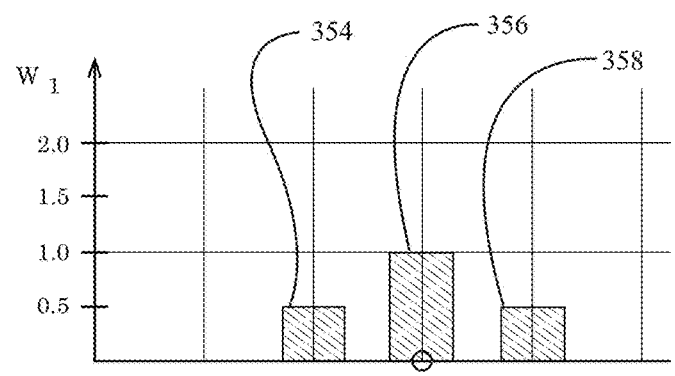
FIG. 11A is a first bar graph illustrating numerical weights applied to the sensor output values of the non-video-based sensors in FIG. 10A.

Next, referring to FIGS. 10A-10C and 11A-11C, an exemplary manner in which the non-video-based sensors may be calibrated so as to compensate for the misalignment of an eye relative to the non-video-based sensors will be described. Initially, as shown in FIG. 10A, the central axis 334 of the eye 322 is shown centered on, and bisecting the dimensional line 328 extending from the center location of the first set of non-video-based sensors 336 to the center location of the second set of non-video-based sensors 338. Because the eye 322 is centered relative to both sets of non-video-based sensors 336, 338 in FIG. 10A, a weight of 1.0 is applied to the centermost sensors 340, 342 of each non-video-based sensor set 336, 338, while a weight of 0.5 is applied to the two sensors disposed on opposite sides of the centermost sensors 340, 342. The weighting of the non-video-based sensors 336, 338 is graphically illustrated in the bar graph 352 of FIG. 11A. As shown in FIG. 11A, the weights of 1.0 that are applied to the centermost sensors 340, 342 are represented by the center bar 356, while the weights of 0.5 that are applied to the two sensors disposed on opposite sides of the centermost sensors 340, 342 are represented by the bars 354, 358.

Figure 11B:
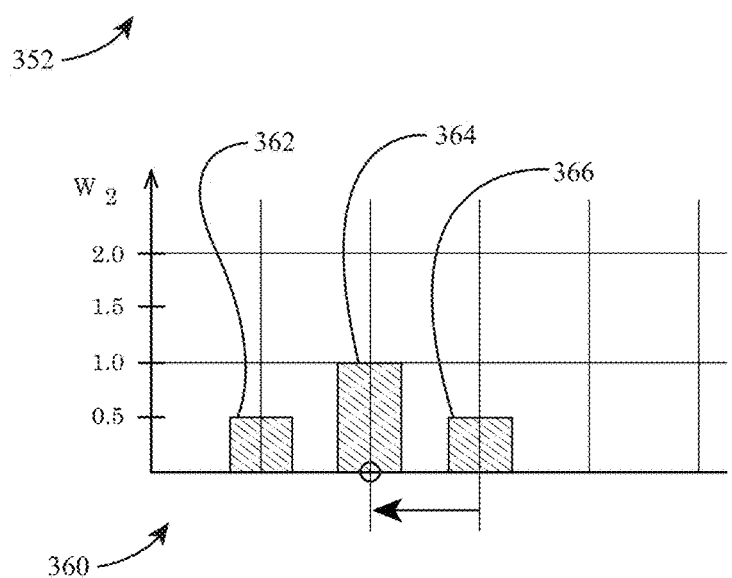
FIG. 11B is a second bar graph illustrating numerical weights applied to the sensor output values of the non-video-based sensors in FIG. 10B.

Turning FIG. 10B, the central axis 334 of the eye 324 is shown offset to the left of the midpoint of the dimensional line 328 by a first distance 330. Because the eye 324 is misaligned to the left relative to both sets of non-video-based sensors 336, 338 in FIG. 10B, a weight of 1.0 is applied to the sensors 344, 346 of each non-video-based sensor set 336, 338, while a weight of 0.5 is applied to the two sensors disposed on opposite sides of the sensors 344, 346. The weighting of the non-video-based sensors 336, 338 is graphically illustrated in the bar graph 360 of FIG. 11B. As shown in FIG. 11B, the weights of 1.0 that are applied to the sensors 344, 346 are represented by the bar 364, while the weights of 0.5 that are applied to the two sensors disposed on opposite sides of the sensors 344, 346 are represented by the bars 362, 366.

Figure 11C:
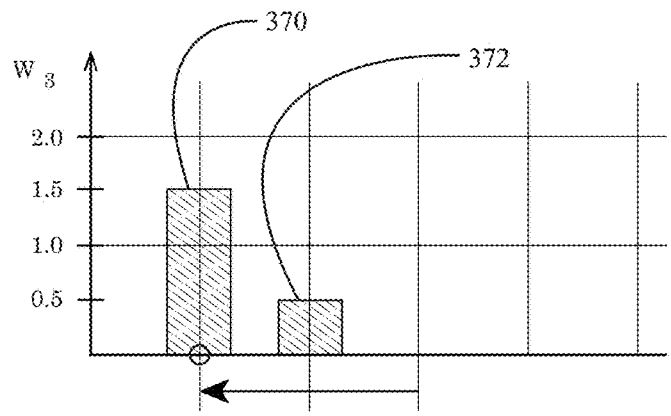
FIG. 11C is a third bar graph illustrating numerical weights applied to the sensor output values of the non-video-based sensors in FIG. 10C.

Next, as shown in FIG. 10C, the central axis 334 of the eye 326 is shown offset to the left of the midpoint of the dimensional line 328 by a second distance 332, which is greater than the offset distance 330 of FIG. 10B. Because the eye 326 is misaligned to the left relative to both sets of non-video-based sensors 336, 338 in FIG. 10C by a greater distance than that of FIG. 10B, a weight of 1.5 is applied to the leftmost sensors 348, 350 of each non-video-based sensor set 336, 338, while a weight of 0.5 is applied to the sensors disposed on right sides of the sensors 348, 350. The weighting of the non-video-based sensors 336, 338 is graphically illustrated in the bar graph 368 of FIG. 11C. As shown in FIG. 11C, the weights of 1.5 that are applied to the sensors 348, 350 are represented by the bar 370, while the weights of 0.5 that are applied to the sensors disposed on right sides of the sensors 348, 350 are represented by the bar 372.

In the embodiment of FIGS. 10A-10C and 11A-11C, the misalignment of the eye relative to the non-video-based sensors is compensated for by selectively applying weights to particular sensors in sensor sets. Although, in other embodiments, the misalignment of the eye relative to the non-video-based sensors may be compensated for by translating and/or rotating the non-video-based sensors using actuators based upon the information obtained from the video-based sensor(s).

Referring again to FIG. 3, it can be seen that, in the illustrative embodiment, the eye movement measurement device 200 further comprises a target generation device (e.g., a target light source 208) mounted on the support frame 232. The target generation device 208 is configured to generate a target and project the target onto a surface (e.g., a wall surface) in front of the user such that the target is visible by the eyes 10, 20 of the user. The target generation device 208 may be in the form of a laser light source or a light emitting diode.

In addition, in one or more embodiments, the eye movement measurement device 200 further comprises a data storage device mounted on the support frame 232. The data storage device comprises non-volatile data storage means, and is configured to store eye movement data so as to enable the eye movement data to be subsequently downloaded to a remote computing device.

The data processing device 136 of the eye movement measurement device 200 is the same as that described above for the first embodiment. In the illustrative embodiment, the data processing device 136 is operatively coupled to the light sources 210, 212, 214, 216, the pair of video-based sensors 202, 204, the pair of non-video-based sensors 218, 220, the target light source 208 and the head position detection device 244 by means of a wireless connection. In an alternative embodiment, the data processing device 136 may be operatively coupled to the light sources 210, 212, 214, 216, the pair of video-based sensors 202, 204, the pair of non-video-based sensors 218, 220, the target light source 208 and the head position detection device 144 by means of a hardwired connection.

In the illustrative embodiment, the eye movement measurement devices 100, 200 are configured to determine the gaze direction of a subject. Once the subject has been outfitted with the eye movement measurement device 100, 200, the eye movement of the subject is determined based upon the output data from the video-based sensors 102, 104, 202, 204 and the non-video-based sensors 118, 120, 218, 220 of the eye movement tracking device 100, 200, while the head position of the subject is determined based upon the output data from the head position detection device 144. The gaze direction of the subject is generally equal to the sum of the head movement and the eye movement, and is given in degrees per second.

The eye movement measurement devices 100, 200 described above may be used for a variety of different eye tests. For example, the eye movement measurement devices 100, 200 may be used in head impulse testing in which the subject's head is moved rapidly either in the horizontal or vertical planes. The examining clinician or physician stands behind the subject while holding the head. The subject is instructed to stare at a stationary dot placed about one meter straight ahead. During several rapid head movements either horizontally (right-left) or vertically (up-down), the eye and head velocities will be determined by the device and used to quantify the performance of the semicircular canals within the vestibular system.

Figure 12:
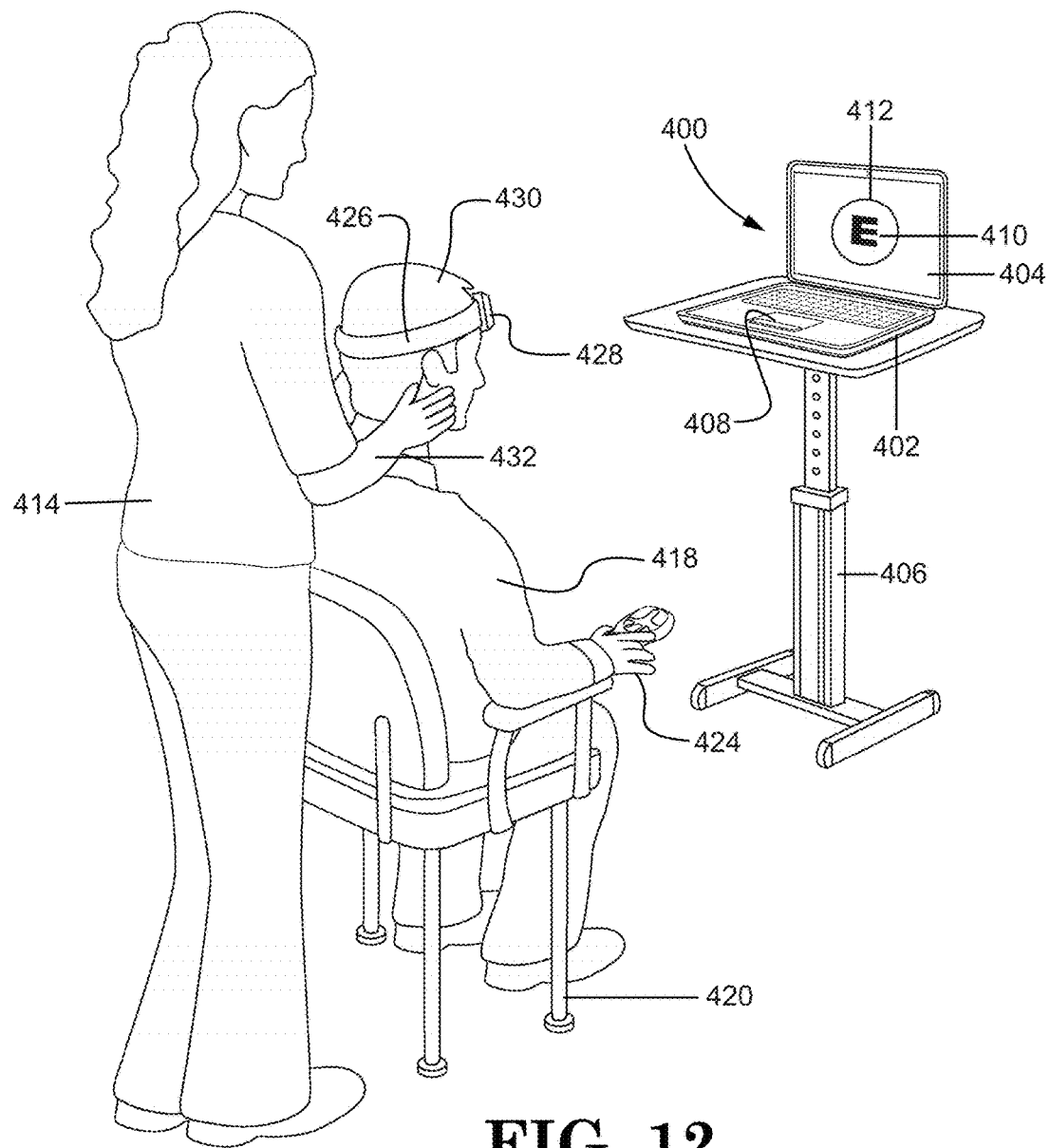
FIG. 12 is a diagrammatic perspective view of a first exemplary vision testing system that utilizes a laptop computing device, according to a further embodiment of the invention.

In one or more further embodiments, a vision testing system is disclosed that is particularly configured for head impulse testing on a subject. An illustrative embodiment of a vision testing system for head impulse testing is seen generally at 400 in FIG. 12. In the illustrative embodiment, the vision testing system 400 generally comprises a laptop computing device 402 with a visual display device 404. The laptop computing device 402 is one exemplary form of a data processing device and/or data processing and data acquisition device. In FIG. 12, the laptop computing device 402 is disposed on an adjustable height table 406 so that the height of the laptop computing device 402 is selectively adjustable by a user. In one or more embodiments, the height of the table 406 is adjusted prior to each test session such that the center of the visual display device 404 of the laptop computing device 402, which contains the one or more visual objects 410, is generally horizontally aligned with the eyes of the subject 418 (i.e., so the subject 418 is looking straight at the visual object 410 on the visual display device 404 during the testing).

The one or more visual objects 410 (e.g., optotypes), which the subject identifies during each vision test described herein, are displayed on the visual display device 404 of the laptop computing device 402 in the illustrative embodiment. Specifically, as shown in FIG. 12, the visual object 410 is displayed on the output screen of the laptop visual display device 404 within a circle 412. The circle 412 circumscribes the visual object 410 and focuses the attention of the subject 418 on the central region of the output screen containing the visual object 410.

While a circle 412 is used to circumscribe the visual object 410 in the illustrative embodiment of FIG. 12, it is to be understood that other suitable shapes could be used to circumscribe the visual object 410 as well. For example, the visual object 410 may be alternatively circumscribed by a square or rectangle, as these shapes are also capable of effectively focusing the subject's attention on the central region of the output screen of the visual display device 404 containing the visual object 410.

In addition, while the visual object 410 in FIG. 12 is in the form of a Tumbling E optotype, it is to be understood that other suitable visual objects 410 may be used in place of the Tumbling E. For example, the visual object 410 alternatively may comprise a Landolt C optotype or an optotype comprising different letters of a recognized alphabet (e.g., different letters of the English alphabet). That is, in some embodiments, the subject 418 may identify different letters of a recognized alphabet, rather than different orientations of the same letter or optotype. Also, in other embodiments, the visual object 410 alternatively may comprise any other identifiable symbol (e.g., a crescent, a star, etc.).

In one or more embodiments, different letters or objects may be displayed in succession during a particular test (e.g., during the head impulse test described hereinafter). For example, during a particular test, a Tumbling E optotype may be displayed first, then followed by the letter "K", a crescent symbol, a star symbol, etc. In this exemplary fashion, the letters that are displayed to the subject 418 can be consistently varied during the performance of the testing.

Referring again to FIG. 12, it can be seen that the head 430 of the subject 418 is fitted with a motion sensing device 428 disposed thereon. In particular, in the illustrative embodiment, the motion sensing device 428 is removably coupled to the head of the subject 418 using a stretchable, elastic headband 426 (i.e., a resilient band 426). The motion sensing device 428 is configured to measure a velocity or speed of the head 430 of the subject 418 when the head 430 of the subject 418 is displaced by the clinician 414 during the head impulse test described herein. That is, the motion sensing device 428 determines the velocity of the subject's head 430 during head impulse test (e.g., the angular velocity of the subject's head 430 in degrees per second).

In the illustrative embodiment, the motion sensing device 428 may comprise a three-dimensional motion sensing device (i.e., an inertial measurement unit (IMU)) having a 3-axis accelerometer, a 3-axis rate gyroscope, and a 3-axis compass (i.e., a 3-axis magnetometer). Also, the illustrative motion sensing device 428 may comprise a wireless data connection to the laptop computing device 402. In particular, the laptop computing device 402 may comprise a data transmission interface unit that is operatively connected to one of the output ports of the laptop computing device 402, such as the universal serial bus (USB) port of the laptop computing device 402. As such, the laptop computing device 402 provided with the data transmission interface unit wirelessly communicates with the motion sensing device 428 using a local wireless network. In addition, the exemplary motion sensing device 428 is both lightweight (e.g., less than 30 grams) and compact in size (e.g., less than 40 mm by 70 mm by 20 mm) so that it is generally comfortable for the subject 418 to wear on his or her head 430.

Next, referring to FIG. 15, an explanation of the three (3) directions of head rotation that the motion sensing device 428 is capable of detecting will be described. First, the motion sensing device 428 is configured to detect the rotation of the head 430 of the subject 418 about the yaw axis 466 of rotation as indicated by the curved arrow 472 in FIG. 15. The curved arrow 472 about the yaw axis 466 indicates the common side-to-side movement of the subject's head 430 during the vision testing. Secondly, the motion sensing device 428 is configured to detect the rotation of the head 430 of the subject 418 about the pitch axis 462 of rotation as indicated by the curved arrow 468 in FIG. 15. The curved arrow 468 about the pitch axis 462 indicates the up-and-down movement of the subject's head 430 during the vision testing. Thirdly, the motion sensing device 428 is configured to detect the rotation of the head 430 of the subject 418 about the roll axis 464 of rotation as indicated by the curved arrow 470 in FIG. 15. The curved arrow 470 about the roll axis 464 indicates the tilt-right and tilt-left movement of the subject's head 430 during the vision testing. In addition to the ability to determine head rotation about all three (3) axes of rotation, the use of a three-dimensional motion sensing device 428 advantageously permits the determination of whether the subject 418 is rotating his or her head 430 purely about the desired axis of rotation (e.g., the yaw axis) or whether there is also off-axis rotation of the subject's head 430 during the prescribed rotation (e.g., the subject is rotating his or head 430 about a combination of the yaw axis and the roll axis, or about a combination of the yaw axis and the pitch axis). Because off-axis rotation may adversely affect the accuracy of the vision testing results, it is important to determine if off-axis rotation is present during the vision testing of the subject 418. The utilization of a three-dimensional motion sensing device 428 enables the determination of this off-axis rotation.

Now, an illustrative manner in which the computing device 402 of the vision testing system 400 performs the head rotation calculations from the output of the motion sensing device 428 will be explained in detail. In particular, this calculation procedure will describe the manner in which the angular position and the angular velocity of the head of the subject 418 may be determined using the signals from the motion sensing device 428 (i.e., the head-mounted IMU) of the vision testing system 400. As explained above, in one or more embodiments, the motion sensing device 428 may be in the form of an IMU, which includes the following three triaxial sensor devices: (i) a three-axis accelerometer sensing linear acceleration $\vec{a}'$, (ii) a three-axis rate gyroscope sensing angular velocity $\vec{w}'$, and (iii) a three-axis magnetometer sensing the magnetic north vector $\vec{n}'$. The motion sensing device 428 (i.e., the IMU) senses in the local (primed) frame of reference attached to the IMU itself. Because each of the sensor devices in the IMU is triaxial, the vectors $\vec{a}'$, $\vec{w}'$, $\vec{n}'$ are each 3-component vectors. A prime symbol is used in conjunction with each of these vectors to symbolize that the measurements are taken in accordance with the local reference frame. The unprimed vectors that will be described hereinafter are in the global reference frame.

The objective of these calculations is to find the angular position or orientation $\vec{\theta}(t)$ and the angular velocity $\vec{w}(t)$ of the head of the subject 418 in the global, unprimed, inertial frame of reference. The initial orientation in the global frame of reference may be either known in advance or derived from $\vec{\Theta}_0$, as will be explained below with regard to the rotation transformation matrix.

For the purposes of the calculation procedure, a right-handed coordinate system is assumed for both global and local frames of reference. The global frame of reference is attached to the Earth. The acceleration due to gravity is assumed to be a constant vector g. Also, for the purposes of the calculations presented herein, it is presumed the sensor devices of the inertial measurement unit (IMU) provide calibrated data. In addition, all of the one or more output signals from the IMU are treated as continuous functions of time. Although, it is to be understood the general form of the equations described herein may be readily discretized to account for IMU sensor devices that take discrete time samples from a bandwidth-limited continuous signal.

The angular velocity $\vec{w}(t)$ of the subject's head rotation is obtained by coordinate transformation using the IMU output signal(s) as follows:

$$\vec{w}(t) = \vec{\Theta}(t)\vec{w}'(t) \quad (2)$$

where $\vec{\Theta}(t)$ is the matrix of the rotation transformation that rotates the instantaneous local frame of reference into the global frame of reference.

The orientation $\vec{\Theta}(t)$ of the subject's head rotation is obtained by single integration of the angular velocity using the IMU output signal(s) as follows:

$$\vec{\theta}(t) = \vec{\theta}_0 + \int_0^t \vec{\omega}(t)\,dt \quad (3)$$

$$\vec{\theta}(t) = \vec{\theta}_0 + \int_0^t \vec{\Theta}(t)\vec{\omega}'(t)\,dt \quad (4)$$

There are two aspects to the coordinate transformation matrix $\vec{\Theta}(t)$ calculation: (i) the initial value $\vec{\Theta}_0 = \vec{\Theta}(0)$ at t=0 and (ii) subsequent updates to this value. The updates may be integrated from the angular velocity, i.e., the time derivative $\dot{\Theta}$ of the rotation transformation matrix may be set as a function of the angular velocity, and then the coordinate transformation matrix becomes:

$$\vec{\Theta}(t) = \int_0^t \Theta(\tau, \vec{\omega}'(\tau))d\tau \quad (5)$$

The value at any point in time may be derived from known local and global values of both the magnetic north vector and the acceleration of gravity. Those two vectors are usually non-parallel. This is the requirement for the $\vec{\Theta}(\vec{g}', \vec{n}', \vec{g}, \vec{n})$ to be unique. The knowledge of either of those vectors in isolation gives a family of non-unique solutions $\vec{\Theta}(\vec{g}', \vec{g})$ or $\vec{\Theta}(\vec{n}', \vec{n})$. Both are unconstrained in one component of rotation. The $\sqrt{\Theta}(\vec{g}'', \vec{n}', \vec{g}, \vec{n})$ has many known implementations, with the common one being the Kabsch algorithm.

In one or more embodiments, if a known starting global orientation is assumed, and the time-derivative of the rotation transformation matrix as a function of the angular velocity in the local frame is used, it is possible to obtain the matrix without the need for the accelerometer and magnetometer in the IMU.

Advantageously, in one or more embodiments, the motion sensing device 428 described above requires no manual calibration step or setup time, other than putting the device 428 on the head 430 of the subject 418. That is, there is no required manual calibration and/or tare step (e.g., to calibrate the accelerometer with respect to gravity and/or to zero the gyroscope) that must be performed prior to the execution of a particular test (i.e., the head impulse test). Obviating the need for manual calibration and/or a manual tare step advantageously saves valuable time during the execution of a particular test series. In order to avoid these laborious and tedious manual steps, at the beginning of every head impulse test trial, the motion sensing device 428 (i.e., inertial measurement unit 428) is automatically re-tared (or re-zeroed) to the subject's head position at that time by the computing device 402. With each of these zeroing events, the computing device 402 also checks the orientation of the motion sensing device 428 in order to make sure that it is on the subject's head 430 correctly and/or to make sure the subject 418 is still and has his or her head held in the correct orientation. The computing device 402 checks the orientation of the motion sensing device 428 by using the data from the linear accelerometer, and by determining which axis the gravity vector lies in. If the computing device 402 detects no issues with the orientation of the motion sensing device 428, nothing happens on the screen (i.e., no message is displayed in order to save time). Conversely, if the computing device 402 determines that there is a problem with the orientation of the motion sensing device 428, a flag pops up on the screen and the test will not begin (i.e., the head impulse test will not begin). In order to begin the test, the clinician must adjust the motion sensing device 428 or the subject's head 430 to the correct position and press "okay" on the keyboard of the computing device 402 to dismiss the flag. Upon the "okay" input, the motion sensing device 428 will tare to its position at that time and the test will begin. In these one or more embodiments, the flag only pops up once per trial.

Also, advantageously, in these one or more embodiments, the motion sensing device 428 does not require a flat and/or still surface for using the motion sensing device 428 (i.e., the inertial measurement unit). In addition, in these one or more embodiments, the motion sensing device 428 does not comprise an electrical cord that operatively connects it to the computing device 402. That is, the motion sensing device 428 is wirelessly coupled to the computing device 402 without the use of any electrical wires. Because the motion sensing device 428 is not tethered (i.e., it contains no electrical cord), it can advantageously accommodate various configurations and distances from the computing device 402. In other words, the configuration of the vision testing system 400 in a room is not limited by the physical limitations imposed upon the system 400 by the fixed length of an electrical cord connecting the motion sensing device 428 to the computing device 402 (e.g., the electrical cord of a tethered motion sensing device 428 may be too short to accommodate a desired testing configuration).

Referring again to FIG. 12, it can be seen that a clinician 414 is standing behind a subject 418 seated on a chair 420. During the head impulse test described herein, wherein the subject's head 430 is to be displaced back-and-forth, the clinician 414 may move the subject's head 430 using her arms 432 so that the velocity and range of motion of the subject's head 430 is capable of being more accurately controlled.

As shown in the illustrative embodiment of FIG. 12, it can also be seen that the subject 418 is holding a user input device 424 in his right hand. The user input device 424 is configured to output an input signal in response to a manipulation of the user input device by a system user (i.e., the subject 418). In the illustrative embodiment, the user input device 424 is operatively coupled to the laptop computing device 402 by wireless data transmission means. For example, the user input device 424 may comprise a wireless mouse that wirelessly communicates with the laptop computing device 402. In other embodiments, the user input device may alternatively comprise (i) a keyboard (e.g., the keyboard of the laptop computing device 402 in FIG. 12), (ii) a wireless clicking device, or (iii) a voice recognition device that allows the subject 418 to verbally input the subject's response (e.g., to record the subject's perceived orientation of the optotype).

Figure 14:
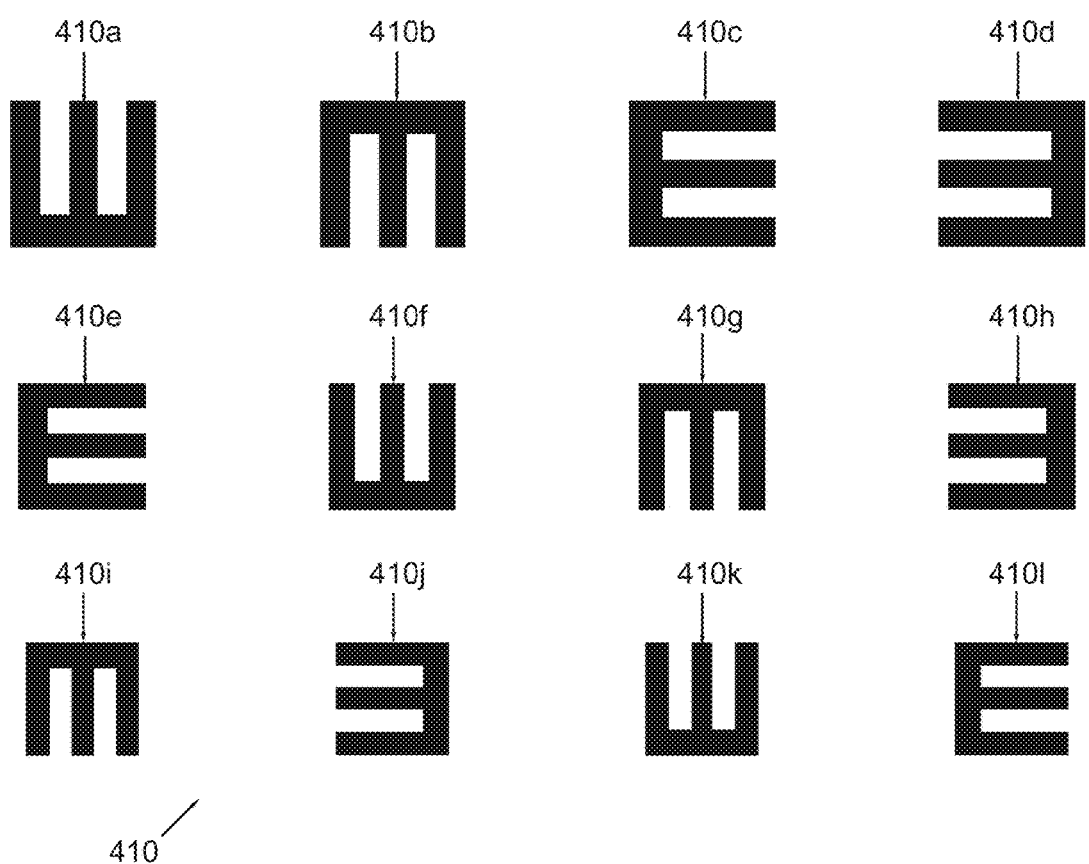
FIG. 14 is an illustration of an exemplary type of optotype that may be utilized in the embodiments of the vision testing systems described herein.

During the vision testing of the subject 418, after the subject 418 identifies the perceived configuration of the visual object 410 that is displayed on the visual display device 404, the subject 418 may use the user input device 424 in order to enter and transmit his or her response (i.e., the perceived configuration of the visual object 410) to the laptop computing device 402. In one or more embodiments, the user input device 424 is configured to accept at least four different responses of the subject 418, wherein each of the at least four different responses of the subject 418 correspond to different configurations of the visual object 410. For example, turning to FIG. 14, it can be seen that, if the visual object 410 is in the form of a Tumbling E optotype, a first configuration of the visual object 410a is one in which the Tumbling E is pointing up (see the top row of FIG. 14), a second configuration of the visual object 410b is one in which the Tumbling E is pointing down, a third configuration of the visual object 410c is one in which the Tumbling E is pointing to the right, and a fourth configuration of the visual object 410d is one in which the Tumbling E is pointing to the left. Next, referring to the middle row of FIG. 14, it can be seen that these same four configurations of the Tumbling E can be displayed on the visual display device 404 in a smaller overall size (e.g., Tumbling E optotypes 410e, 410f, 410g, 410h). Finally, with reference to bottom row of FIG. 14, it can be seen that these same four configurations of the Tumbling E can be displayed on the visual display device 404 in an even smaller overall size (e.g., Tumbling E optotypes 410i, 410j, 410k, 410l).

Figure 13:
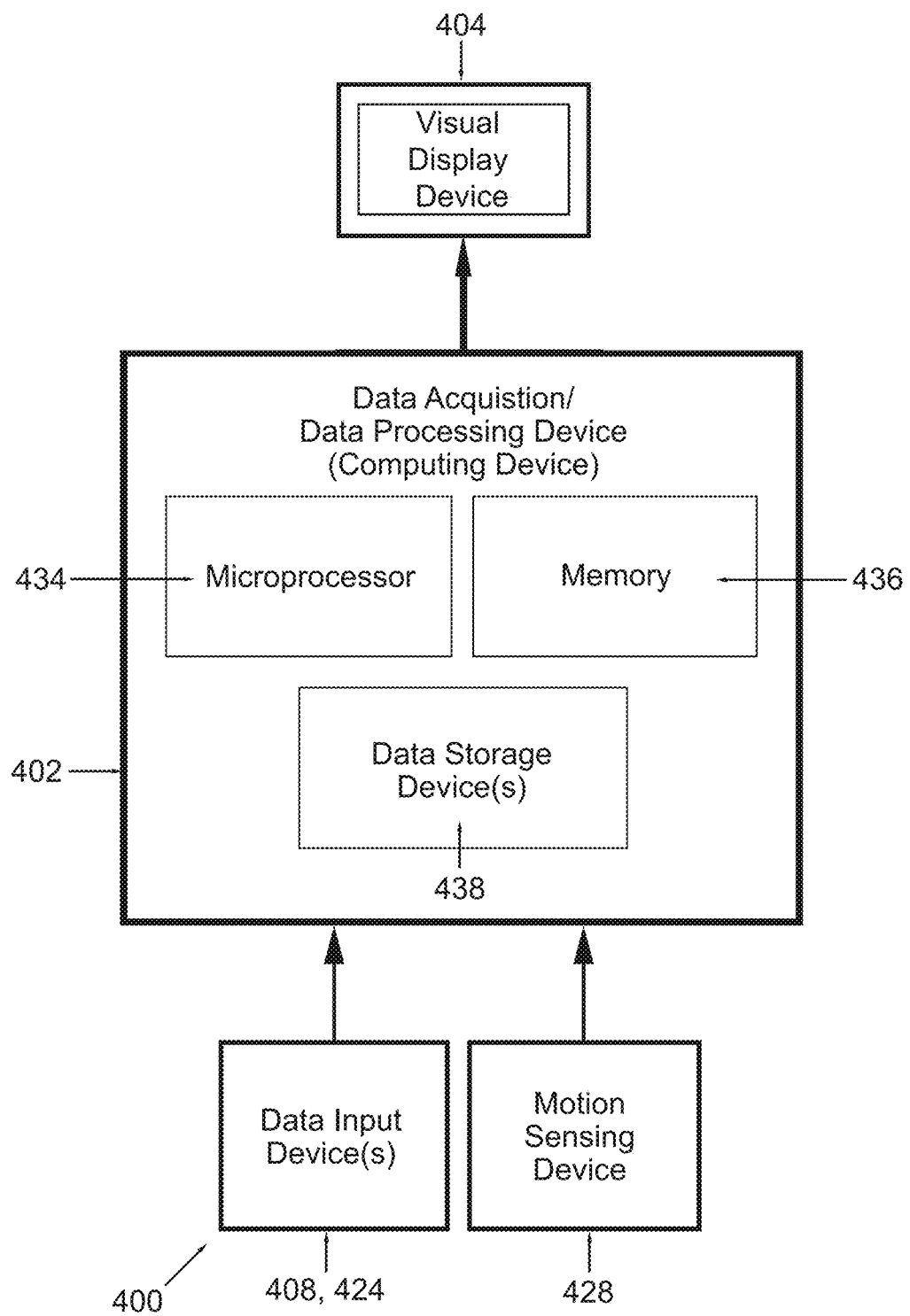
FIG. 13 is a block diagram of constituent components that may be utilized in the embodiment of the vision testing system of FIG. 12.

Now, turning to FIG. 13, it can be seen that the data acquisition/data processing device (i.e., the computing device 402) of the illustrative vision testing system 400 comprises a microprocessor 434 for processing data, memory 436 (e.g., random access memory or RAM) for storing data during the processing thereof, and data storage device(s) 438, such as one or more hard drives, compact disk drives, floppy disk drives, flash drives, or any combination thereof. As shown in FIG. 13, the motion sensing device 428 and the visual display device 404 are operatively coupled to the computing device 402 such that data is capable of being transferred between these devices. Also, as illustrated in FIG. 13, a plurality of data input devices 408, 424, such as the wireless mouse 424, keyboard, and touchpad 408, are operatively coupled to the computing device 402 so that a user is able to enter data into the computing device 402. In some embodiments, the computing device may be in the form of a laptop computer (as shown in FIG. 12), while in other embodiments, the computing device may be embodied as a desktop computer.

Figure 16:
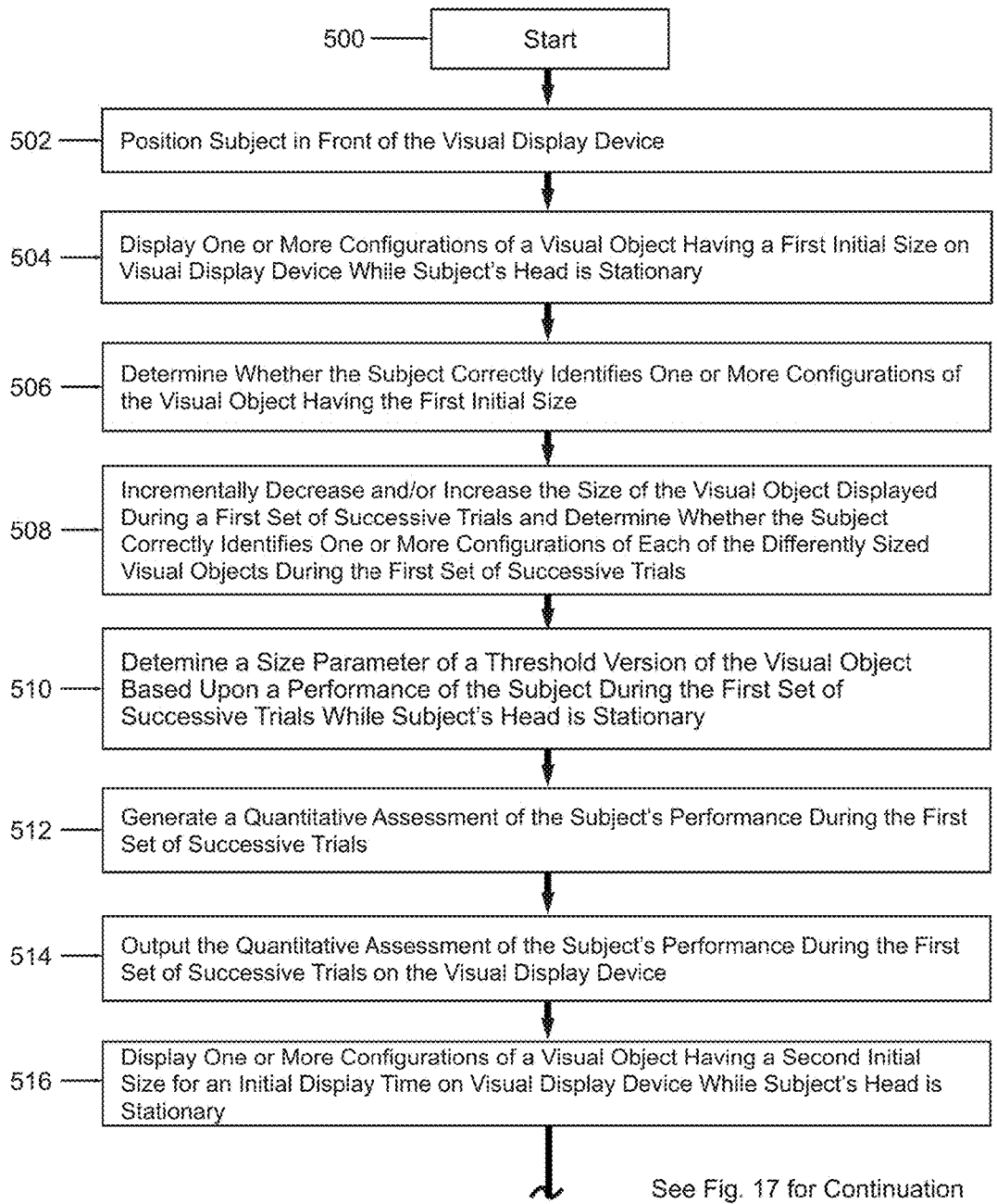
FIG. 16 is a partial flowchart illustrating a procedure for vision testing of a subject carried out by the system illustrated in FIG. 12, according to an embodiment of the invention.
Figure 17:
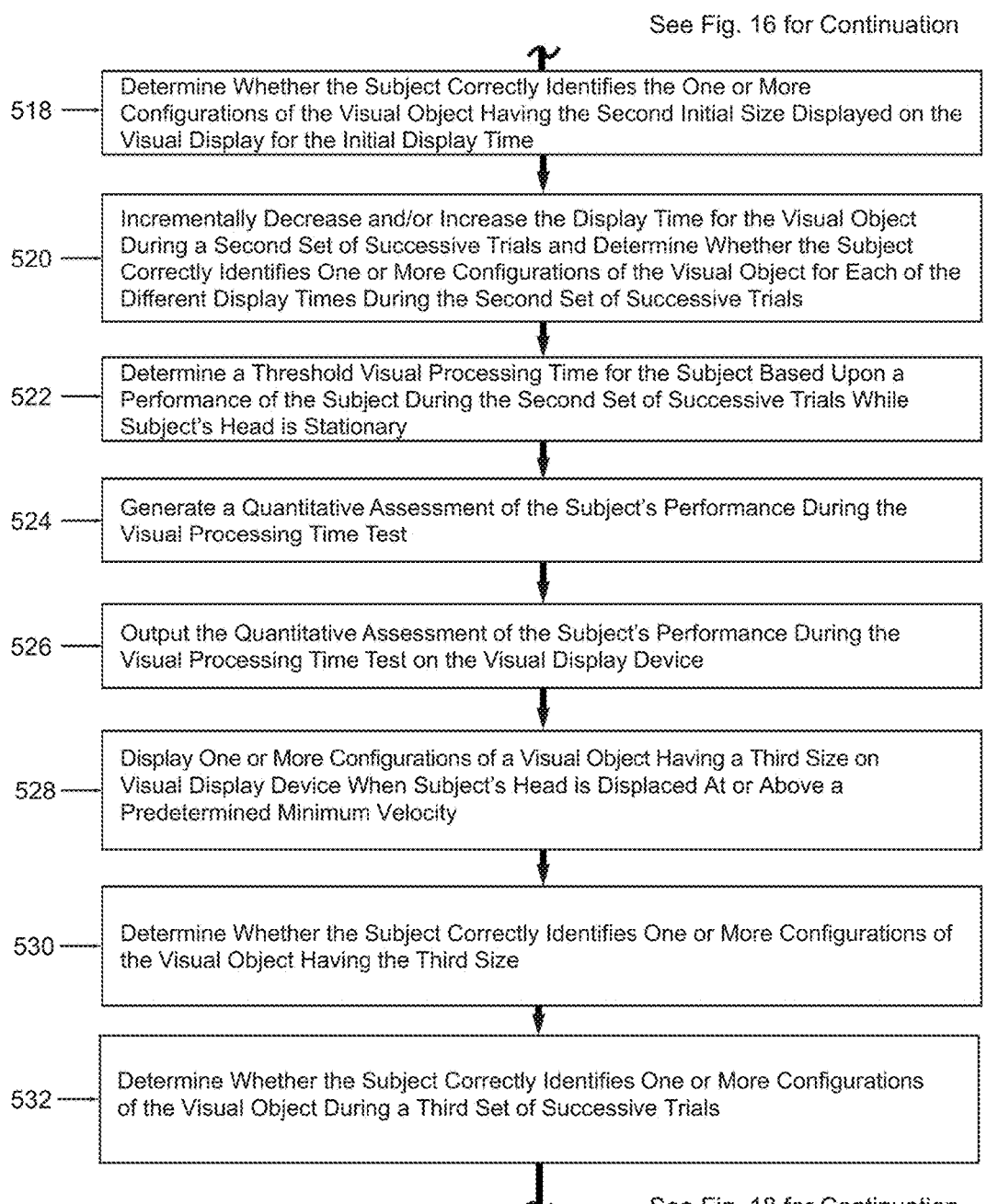
FIG. 17 is a continuation of the flowchart of FIG. 16, which illustrates additional steps of the procedure for vision testing of a subject, according to an embodiment of the invention.
Figure 18:
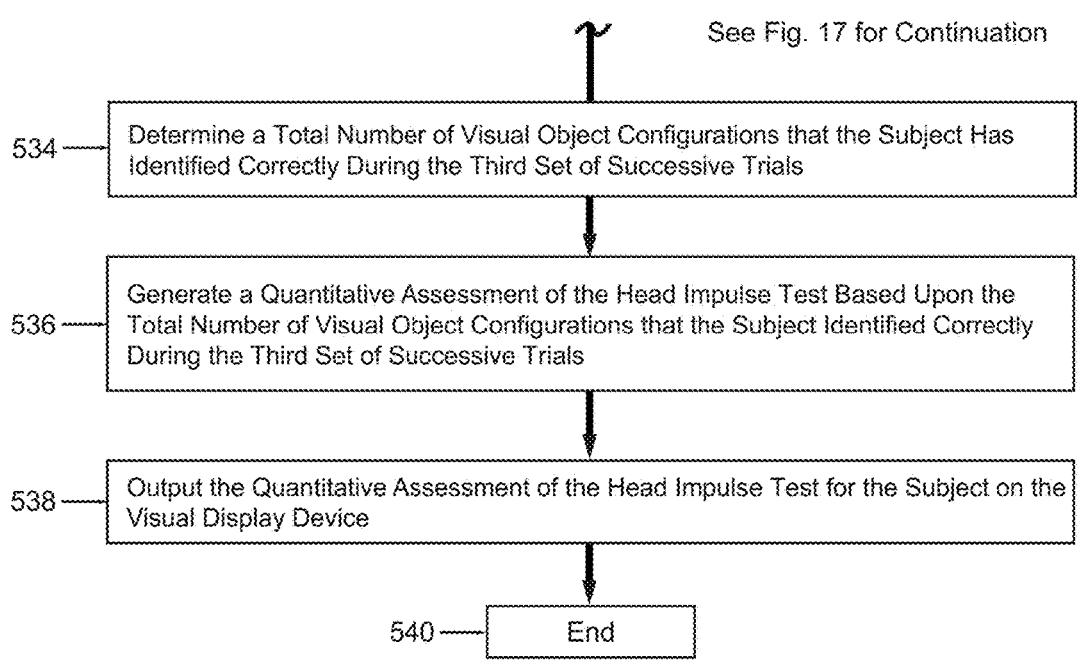
FIG. 18 is a continuation of the flowchart of FIG. 17, which illustrates yet additional steps of the procedure for vision testing of a subject, according to an embodiment of the invention.

In accordance with the illustrative embodiment of the invention, a flowchart illustrating a procedure for head impulse testing of a subject carried out by the system 400 is set forth in FIGS. 16-18. Referring initially to FIG. 16, the procedure commences at 500 (e.g., after the operator or clinician enters a start command to the computing device 402 by depressing a particular key on the keyboard), and in step 502, the subject is positioned in front of the output screen of the visual display device 404 such that a visual object 410 (e.g., an optotype) is visible to the subject 418. Then, while the subject 418 maintains a generally fixed position of his or her head 430 (i.e., keeping his or her head 430 as still as possible), one or more configurations of the visual object 410 having a first initial size are displayed on the output screen of the visual display device 404 in step 504. For example, referring to FIG. 14, one or more configurations 410e, 410f, 410g, 410h of the Tumbling E optotype may be displayed one-at-time on the output screen of the visual display device 404. In other exemplary embodiments, other suitable optotypes may be used in place of the Tumbling E, such as a Landolt C or letters of a recognized alphabet (e.g., the English alphabet). In one or more embodiments, the visual object (i.e., optotype) having the first initial size is displayed within approximately 500 milliseconds after the operator or clinician enters the start command to the computing device 402. The visual object (i.e., optotype) having the first initial size may be sufficiently large so that nearly all of the subjects tested will correctly identify the configuration of the first optotype that is displayed on the screen, and may be displayed for a time duration of approximately 500 milliseconds on the screen. After the visual object (i.e., optotype) disappears from the output screen of the visual display device 404, the computing device 402 may be specially programmed to implement a wait state, wherein the computing device 402 waits to record the subject's response.

Figure 19:
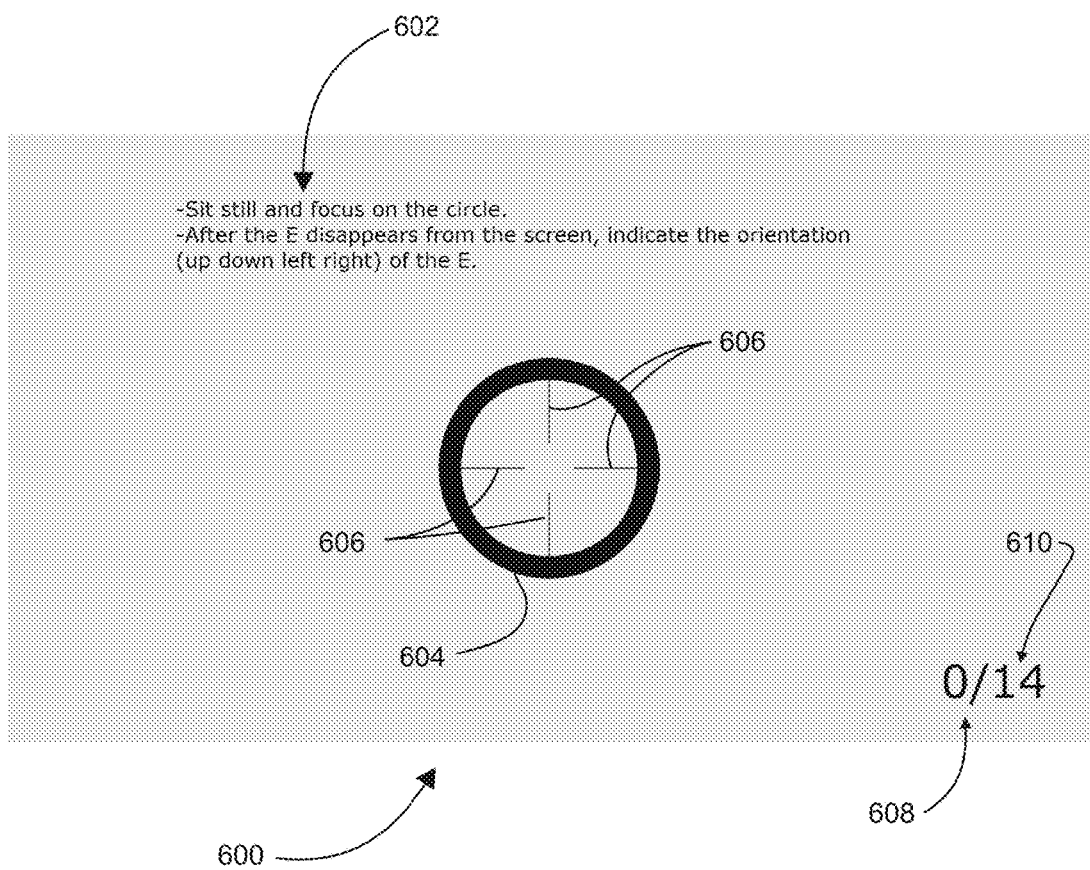
FIG. 19 is a subject screen image of the visual display device with an exemplary visual indicator that may be utilized during the performance of the vision test, according to an embodiment of the invention.
Figure 20:
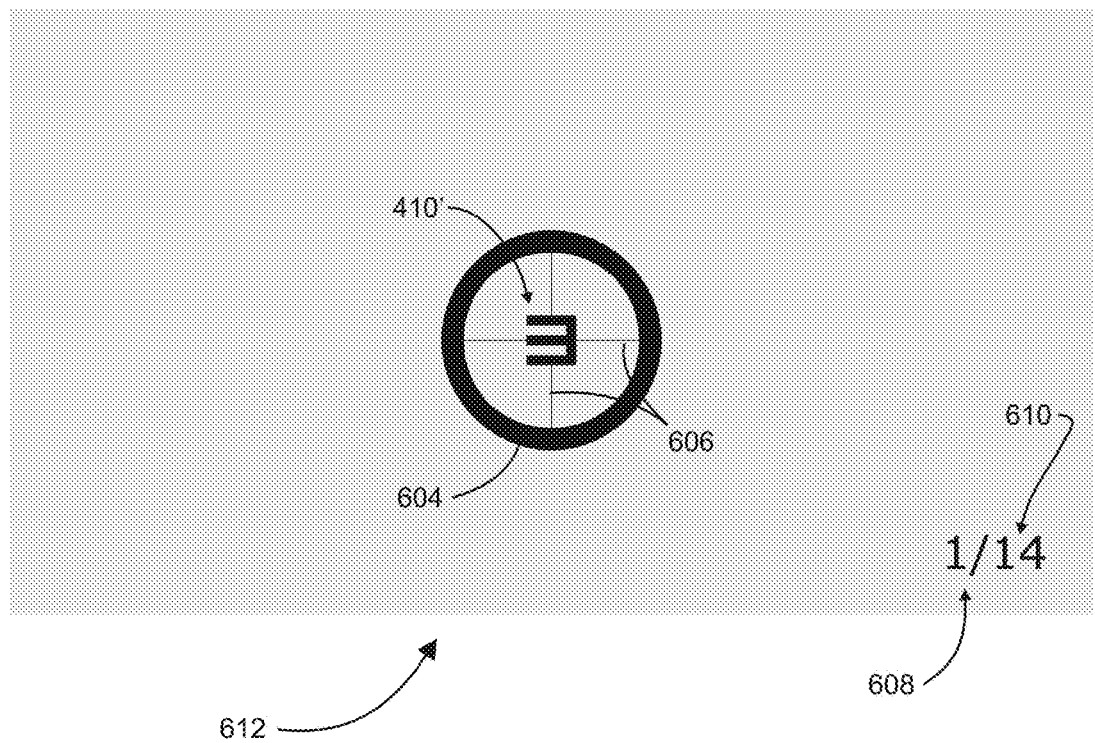
FIG. 20 is a subject test screen image of the visual display device prior to the performance a static visual acuity test or a visual processing time test, wherein the exemplary visual indicator is displayed together with the exemplary optotype, according to an embodiment of the invention.

With reference to FIGS. 19 and 20, exemplary subject screen images 600, 612, which may be displayed on the visual display device 404 during the first set of successive trials when the subject 418 maintains the generally fixed position of his or her head 430, will now be explained. Initially, referring to FIG. 19, it can be seen that a set of instructions 602 for the subject or patient may be displayed at the top of the screen image 600. The subject or patient instructions may specify that the manner in which the subject or patient is supposed to carry out the test (e.g., by instructing the patient to sit still and focus on the circle 604, and by instructing the patient to indicate the orientation of the optotype after it disappears from the screen). The set of instructions 602 may be initially displayed on the output screen by the computing device 402, and then subsequently hid from view (i.e., suppressed thereafter) so as not to unnecessarily distract the subject 418 during the testing. As additionally shown in FIG. 19, a solid black circle 604 is displayed in the approximate center of the screen. The solid black circle 604 comprises a plurality of crosshairs 606 disposed therein (e.g., spaced 90 degrees apart from one another, and disposed at 0 degrees, 90 degrees, 180 degrees, and 360 degrees), and extending inwardly towards the center of the circle 604. Referring again to FIG. 19, it can be seen that, in the bottom right-hand corner of the screen, the number of trials 608 completed thus far, together with the maximum number of trials 610 that may be completed during the first set of successive trials is displayed. Because FIG. 19 depicts the starting screen image 600 for the first set of successive trials (i.e., when the subject's head is stationary), the number 608 is zero (0) in FIG. 19. In this illustrative embodiment, the maximum number of trials 610 performed in conjunction with the first set of successive trials is fourteen (14). However, it is to be understood that, in other embodiments of the invention, the maximum number of trials 610 performed in conjunction with the first set of successive trials may be higher or lower than fourteen (14). Also, in an alternative embodiment, a small box with the optotype size and a small box with the optotype display time may be placed in the bottom right-hand corner of the screen 600, rather than the number of trials 608 completed thus far, and the maximum number of trials 610. In this alternative embodiment, the number of trials 608 completed thus far, and the maximum number of trials 610 may be placed in test summary data on the operator or clinician screen. Turning to FIG. 20, it can be seen that the screen image 612 is generally the same as the screen image 600 of FIG. 19, except that an optotype 410' is displayed in the center of the circle 604. While a Tumbling E optotype is utilized in the illustrative embodiment of FIG. 20, it is to be understood that, in an alternative embodiment, a Landolt C optotype or another type of optotype may be used in place of the Tumbling E optotype. In the exemplary screen image 612 of FIG. 20, it can be seen that the optotype is pointing to the left, so a correct identification of the optotype by the subject or patient would require that he or she indicates that the optotype is pointing to the left. In addition, as depicted in FIG. 20, the number of trials 608 is equal to one (1) in order to indicate that the subject or patient has completed one trial of the first set of successive trials (i.e., when the subject's head is stationary).

The circle 604 depicted in FIGS. 19 and 20, which is generated by the computing device 402, is large enough to fit the largest size optotype that will be displayed to the subject or patient during the static testing. The crosshairs 606 extend inward in order to prevent the circle 604 from needing to change size. Advantageously, in order to avoid becoming a distraction to the subject during the testing, the size of the circle 604 remains constant (i.e., it is static). Because the size of the circle 604 is constant during the testing, it must be large enough to accommodate the largest optotype that will be displayed to the subject during the testing. Consequently, this results in a circle 604 that is significantly larger than the smallest sized optotypes displayed during the testing, which in turn, makes it difficult for the subject to tell where the small sized optotypes will appear on the screen. The subject's ability to find the optotype on the screen is not something that it is desired to be factored into the testing. Thus, the crosshairs 606 are provided within the circle 604 in order to help direct the gaze of the subject or patient during the display of the optotype, especially that of a small optotype. Like the circle 604, the crosshairs 606 are static during the testing (i.e., they do not undergo changes in size or shape) so as not to distract the subject during the testing. Also, as best shown in FIG. 19, the crosshairs 606 do not extend all the way to the center of the circle 604 so as to prevent them from interfering with the display of the small optotypes. In addition, both the circle 604 and the crosshairs 606 remain on the output screen of the visual display device throughout the duration of the testing.

Now, turning again to FIG. 16, in step 506, the computing device or data processing device 402 determines whether or not the subject 418 correctly identifies one or more configurations (e.g., 410*e*, 410*f*, 410*g*, 410*h*) of the visual object 410 having the first initial size. For example, the subject 418 may be presented with one or more optotypes having the first initial size (e.g. a single optotype 410*g* pointing down). This optotype 410*g* is of the first initial size, which may be a size scale factor of 0.75. After the optotype is displayed to the subject 418, the subject 418 may utilize a user input device 424 (e.g., a wireless mouse) in order to transmit the response of the subject 418 to the computing device 402 (e.g., the wireless mouse may have four buttons, each of which corresponds to one of the four configurations of the optotype). Alternatively, the response of the subject 418 may be entered using the keyboard of the computing device 402 by using the directional arrows and space bar on the keyboard. For example, the "up" arrow key on the keyboard is used to record an optotype pointing up, the "down" arrow key on the keyboard is used to record an optotype pointing down, the "left" arrow key on the keyboard is used to record an optotype pointing to the left, the "right" arrow key on the keyboard is used to record an optotype pointing to the right, and the spacebar is used to record an unknown orientation of the optotype. If the spacebar is depressed on the keyboard, the computing device 402 randomly chooses the response of the subject 418. After receiving the subject's response, the computing device 402 is specially programmed to determine if the subject correctly determined the configuration of the optotype that was displayed on the output screen of the visual display device 404. For example, if the optotype 410*g* of FIG. 14 was displayed on the screen, the subject 418 must indicate that optotype is pointing down to get the identification correct. Any other answer would be incorrect for this configuration of the optotype. Once the subject's answer or response is evaluated as to its correctness, the computing device 402 is specially programmed to record whether or not the subject 418 identified the optotype correctly. In one exemplary embodiment, if the subject 418 identifies the configuration of the optotype 410*g* correctly, the computing device 402 is specially programmed to display one or more optotypes having a physical size that is smaller than the first optotype (e.g., the second trial may comprise one or more optotypes that have a size scale factor of 0.6875). For example, the second optotype may comprise the optotype 410*j* in FIG. 14, which has a smaller size than the optotype 410*g* in the middle row of FIG. 14. Conversely, if the subject 418 identifies the configuration of the first optotype 410*g* incorrectly, the computing device 402 is specially programmed to display one or more optotypes having a physical size that is larger than the first optotype (e.g., the second optotype may have a size scale factor of 1.0). For example, in this case, the second optotype may comprise the optotype 410*c* in the top row of FIG. 14, which has a larger size than the optotype 410*g* in the middle row of FIG. 14. In one or more embodiments, as described hereinafter, the computing device 402 is specially programmed to execute a parameter estimation algorithm in order to determine the physical size of the successive optotype that is displayed on the output screen of the visual display device 404. Also, in one or more embodiments, the computing device 402 is specially programmed to display the successive optotype on the screen approximately five-hundred (500) seconds after it receives the subject's response regarding the preceding optotype.

In this manner, as specified in step 508 of FIG. 16, the computing device 402 is specially programmed to incrementally decrease or increase the size of the visual object on the output screen of the visual display device 404 during a first set of successive trials (e.g., during a maximum number 610 of fourteen (14) trials as indicated in FIGS. 19 and 20). For example, if the subject identifies the configuration of a particular-sized optotype correctly, the optotype size of the next optotype displayed on the screen is generally decreased, while the optotype size of the next optotype displayed on the screen is generally increased if the subject fails to identify the configuration of the optotype correctly. In the exemplary embodiment, after each optotype is displayed on the output screen of the visual display device 404, the computing device 402 is specifically programmed to determine whether or not the subject 418 correctly identified the configuration of the optotype.

In one or more embodiments, the size of the visual object presented to the subject 418 during the first set of successive trials generally changes with each successive trial (e.g., the subject 418 does not receive five (5) optotypes of the same size in consecutive order during the testing). In contrast to the static visual acuity testing, the size of the visual object presented to the subject 418 during the head impulse test trials, as described hereinafter, remains constant during each successive trial (e.g., the subject 418 receives optotypes of the same size during the head impulse testing).

In step 510 of FIG. 16, after the subject 418 has completed a predetermined number of trials of optotype identification, the computing device 402 is specifically programmed to determine a size parameter (e.g., a size scale factor) of a first threshold version of the optotype based upon the performance of the subject 418 during the first set of successive trials during which the subject 418 maintained the generally fixed position of his or her head 430. For example, after a particular end condition is reached, the computing device 402 determines that the first threshold version of the optotype has a size scale factor of 0.40. In one embodiment, the size scale factor of the first threshold version of the optotype is a calculated value that is determined using one or more statistical equations or formulas (e.g., using a parameter estimation algorithm as described hereinafter).

The computing device 402 may be specifically programmed with multiple end conditions for determining when to end the first set of successive trials. For example, the computing device 402 may automatically stop the first set of successive trials as soon as any one or combination of the following conditions occur: (i) the subject has completed a total of fourteen (14) trials of optotype identification (i.e., a maximum allowable number of trials is reached), (ii) a predetermined number of reversals has occurred, or (iii) the user has stopped the first set of successive trials (e.g., the operator or clinician initiates the cessation of the successive trials by depressing a particular key on the keyboard).

In one or more embodiments, the computing device 402 may be specially programmed to automatically stop the first set of successive trials when both the computed number of reversals for the test series has exceeded the predetermined number of reversals and the computed number of trials for the test series has exceeded the predetermined number of trials. Initially, the manner in which the total number of reversals is calculated by the computing device 402 will be explained. During the vision testing, a reversal is determined in accordance with the following equation:

$$\text{diff} = [y(i-1) - y(i)] * [y(i) - y(i+1)] \qquad (6)$$

where:
diff: product of the slope before and after a stimulus point;
y(i): stimulus value at trial number i;
y(i−1): stimulus value for the trial preceding trial number i;
y(i+1): stimulus value for the trial following trial number i;
i: trial number for which the reversal is being determined.

After computing the difference value determined using equation (6) for a given trial number, if it is determined by the computing device 402 that the difference value is less than or equal to zero, then the reversal counter is incremented using the following equation:

$$\text{rev} = \text{rev} + 1 \qquad (7)$$

That is, the reversal number counter is incremented by one. Conversely, if it is determined by the computing device 402 that the difference value is greater than zero, then the reversal counter is not incremented and the number of reversals stays the same. Also, if the computed difference value is less than or equal to zero, and thus the reversal counter is incremented, the computing device 402 may be specially programmed to next determine if the total computed number of reversals is greater than or equal to the predetermined number of reversals that has been set (e.g., a total number of eight (8) reversals). After which, the computing device 402 may be specially programmed to further determine if the total number of trials that have been completed (value of i) is greater than or equal to a predetermined number of trials (e.g., fourteen (14) trials of optotype identification). When both the total computed number of reversals is greater than or equal to the predetermined number of reversals (e.g., eight (8) reversals), and the total number of trials that have been completed is greater than or equal to the predetermined number of trials (e.g., fourteen (14) trials), then the computing device 402 may be specially programmed to automatically stop the first set of successive trials of the vision testing. It is to be understood that the abovedescribed procedure may be used to determine the stopping point of the visual processing time, and head impulse test series of successive trials as well.

Then, in step 512 of FIG. 16, the computing device 402 is specifically programmed to generate a quantitative assessment of the subject's performance during the first set of successive trials, and finally, in step 514 of FIG. 16, to output the quantitative assessment of the subject's performance during the first set of successive trials on the output screen of the visual display device 404. For example, in an exemplary embodiment, the computing device 402 may generate a report in order to display the test results from the first set of successive trials.

After determining the size parameter of the first threshold version of the optotype in step 510 above, and generating and displaying the quantitative results in steps 512 and 514, the visual processing time of the subject 418 may be determined by the computing device 402 in steps 516-522 of FIGS. 16 and 17. The purpose of this test is to determine how long the optotype needs to be displayed on the screen of the visual display device 404 in order for the subject 418 to comprehend the displayed orientation of the optotype Like the first set of successive trials described above, the visual processing time test is a static-type test, so there are no head movements made by the subject or patient during the performance of the visual processing time test. The size scale factor of the first threshold version of the optotype (e.g., in units of logMAR or relative logMAR) that was determined in conjunction with the first set of successive trials described above is used by the visual processing time test. In particular, the optotype size during the performance of the visual processing time test is determined by increasing the optotype size determined in conjunction with the first set of successive trials by two sizes (e.g., by 0.2 logMAR). This optotype size remains constant for all trials of the visual processing time test. The variable in the visual processing time test is the time duration during which the optotype is displayed on the screen. The stimulus level (i.e., selected display time of the optotype on the screen) may be determined by the computing device 402 using the same parameter estimation algorithm that selects the optotype size in the first set of successive trials described above.

In one or more exemplary embodiments, during the visual processing time test, the shortest amount of time that the optotype is displayed on the screen of the visual display device 404 is twenty (20) milliseconds (i.e., because of the monitor refresh rate), while the maximum amount of time that the optotype is displayed on the screen of the visual display device 404 is seventy (70) milliseconds. The upper limit of seventy (70) milliseconds was selected because, if the subject or patient has a visual processing time greater than 70 milliseconds he or she will be unable to complete the dynamic trials of the head impulse test. An individual with a visual processing time greater than 70 milliseconds would be unable to complete these dynamic trials because the optotype must be displayed on the visual display device 404 while the head of the subject or patient is being displaced. If the display time of the optotype needed to be much longer than 70 milliseconds, it would not be possible to display the optotype only during the subject's head movement, and conversely, to not display it when the subject's head is at maximum amplitude and head velocity is zero (0).

In one or more embodiments, the computing device 402 may be specially programmed to prompt the operator or clinician to input the step change (i.e., resolution) in the visual processing time between trials. The default test setting for the resolution may be ten (10) milliseconds, while the computing device 402 may be specially programmed to accept a resolution range between ten (10) milliseconds and fifty (50) milliseconds, inclusive.

After the operator or clinician enters a start command to the computing device 402 by depressing a particular key on the keyboard, the visual processing time test begins. Turning again to the flowchart of FIG. 16, it can be seen in step 516 that, while the subject 418 maintains a generally fixed position of his or her head 430 (i.e., keeping his or her head 430 as still as possible), one or more configurations of the visual object 410 are displayed on the output screen of the visual display device 404 for an initial display time (e.g., the optotype is displayed for ninety (90) milliseconds on the screen). For example, referring to FIG. 14, one or more configurations 410*a*, 410*b*, 410*c*, 410*d* of the Tumbling E optotype may be displayed one-at-time on the output screen of the visual display device 404 for an initial display time.

In an alternative exemplary embodiment, one or more configurations of a Landolt C optotype may be displayed one-at-time on the output screen of the visual display device 404 for an initial display time. In other exemplary embodiments, other suitable optotypes may be used in place of the Tumbling E or Landolt C, such as letters of a recognized alphabet (e.g., the English alphabet). In one or more embodiments, the visual object 410 (i.e., optotype) is displayed in approximately 500 milliseconds after the operator or clinician enters the start command to the computing device 402. After the visual object (i.e., optotype) disappears from the output screen of the visual display device 404, the computing device 402 may be specially programmed to implement a wait state, wherein the computing device 402 waits for the subject or clinician to record the subject's response.

During the visual processing time test, the same solid black circle 604 and crosshairs 606, which was described above in conjunction with FIGS. 19 and 20, is used to present the optotype to the subject 418. That is, the patient screen during the visual processing time test is generally the same as the screen images 600, 612 in FIGS. 19 and 20.

Now, with reference to FIG. 17, in step 518, the computing device or data processing device 402 determines whether or not the subject 418 correctly identifies the one or more configurations (e.g., 410a, 410b, 410c, 410d) of the visual object 410 that is displayed on the visual display device 404 for the initial display time. For example, the subject 418 may be presented with a single optotype 410b pointing down (see FIG. 14). After the optotype is displayed to the subject 418, the subject 418 or the clinician 414 may utilize a user input device 424 (e.g., a wireless mouse) in order to transmit the response of the subject 418 to the computing device 402 (e.g., the wireless mouse may have four buttons, each of which corresponds to one of the four configurations of the optotype). Alternatively, the response of the subject 418 may be entered using the keyboard of the computing device 402 by using the directional arrows and space bar on the keyboard. For example, the "up" arrow key on the keyboard is used to record an optotype pointing up, the "down" arrow key on the keyboard is used to record an optotype pointing down, the "left" arrow key on the keyboard is used to record an optotype pointing to the left, the "right" arrow key on the keyboard is used to record an optotype pointing to the right, and the spacebar is used to record an unknown orientation of the optotype. If the space bar is depressed on the keyboard, the computing device 402 randomly chooses the response of the subject 418. After receiving the subject's response, the computing device 402 is specially programmed to determine if the subject correctly determined the configuration of the optotype that was displayed on the output screen of the visual display device 404. For example, if the optotype 410b of FIG. 14 was displayed on the screen, the subject 418 must indicate that optotype is pointing down to get the identification correct. Any other answer would be incorrect for this configuration of the optotype. Once the subject's answer or response is evaluated as to its correctness, the computing device 402 is specially programmed to record whether or not the subject 418 identified the optotype correctly. In one exemplary embodiment, if the subject 418 identifies the configuration of the optotype 410b correctly, the computing device 402 is specially programmed to display one or more subsequent optotypes for a display time that is shorter than the initial display time (e.g., the second trial may display the subsequent optotype on the screen for a display time of only 50 milliseconds, rather than the 60 milliseconds that was used during the initial trial). Conversely, if the subject 418 identifies the configuration of the first optotype 410b incorrectly, the computing device 402 is specially programmed to display one or more subsequent optotypes for a display time that is longer than the initial display time (e.g., the second trial may display the subsequent optotype on the screen for a display time of 70 milliseconds, rather than the 60 milliseconds that was used during the initial trial). Also, in one or more embodiments, the computing device 402 is specially programmed to display the successive optotype on the screen approximately five-hundred (500) milliseconds after it receives the subject's response regarding the preceding optotype.

In this manner, as specified in step 520 of FIG. 17, the computing device 402 is specially programmed to incrementally decrease or increase the display time for the visual object on the output screen of the visual display device 404 during a set of successive trials (e.g., during a maximum number 610 of fourteen (14) trials as indicated in FIGS. 19 and 20). During the set of successive trials, various configurations of the same-sized visual object may be displayed on the output screen of the visual display device 404 for identification by the subject. For example, if the subject identifies a configuration of the same-sized optotype correctly, the screen display time for next-displayed optotype is generally decreased, while the screen display time for next-displayed optotype is generally increased if the subject fails to correctly identify the configuration of the optotype correctly. In the exemplary embodiment, after each optotype is displayed on the output screen of the visual display device 404 for a particular display time, the computing device 402 is specifically programmed to determine whether or not the subject 418 correctly identified the configuration of the optotype. In step 522 of FIG. 17, after the subject 418 has completed a predetermined number of trials of optotype identification, the computing device 402 is specifically programmed to determine a threshold visual processing time for the subject 418 based upon the performance of the subject 418 during the set of successive trials during which the subject 418 maintained the generally fixed position of his or her head 430. For example, after a particular end condition is reached, the computing device 402 determines that the visual processing time for the subject 418 is fifty-five (55) milliseconds. In one embodiment, the visual processing time for the subject 418 is a calculated value that is determined using one or more statistical equations or formulas (e.g., using a parameter estimation algorithm as described hereinafter).

As described above for the first set of successive trials, the computing device 402 may be specifically programmed with multiple end conditions for determining when to end the second set of successive trials. For example, the computing device 402 may automatically stop the second set of successive trials as soon as any one or combination of the following conditions occur: (i) the subject has completed a total of fourteen (14) trials of optotype identification (i.e., a maximum allowable number of trials is reached), (ii) a predetermined number of reversals has occurred (refer to explanation above), or (iii) the user has stopped the first set of successive trials (e.g., the operator or clinician initiates the cessation of the successive trials by depressing a particular key on the keyboard).

Then, in step 524 of FIG. 17, the computing device 402 is specifically programmed to generate a quantitative assessment of the subject's performance during the visual processing time test, and finally, in step 526 of FIG. 17, to output the quantitative assessment of the subject's performance during the visual processing time test on the output screen of the visual display device 404. For example, in an exemplary embodiment, the computing device 402 may generate a report in order to display the test results from the visual processing time test.

Figure 21:
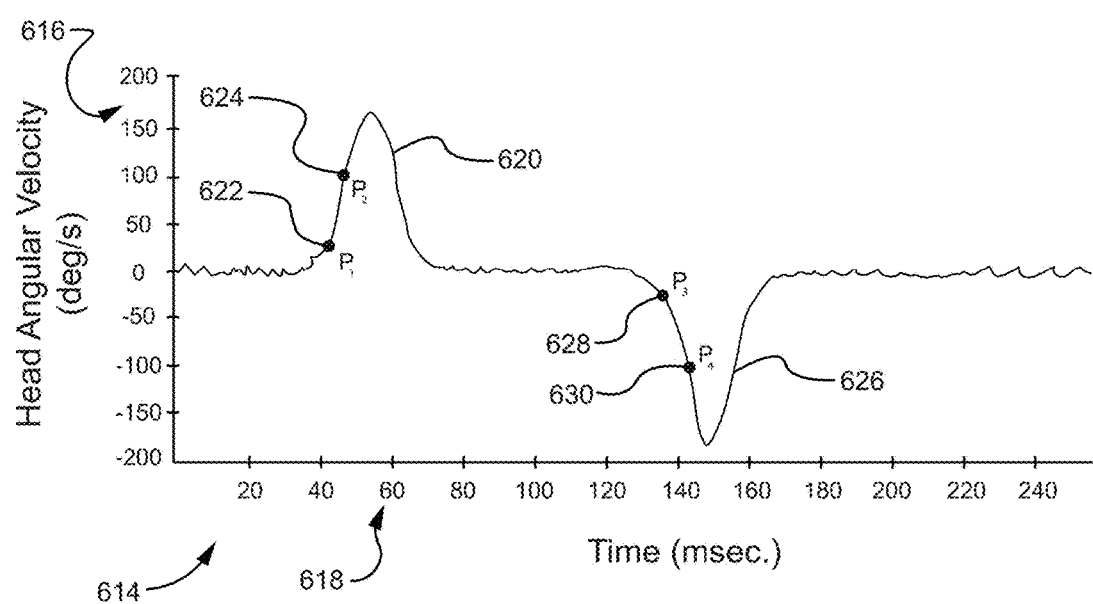
FIG. 21 is a graph illustrating a head angular velocity curve generated during the performance of a head impulse test, according to an embodiment of the invention.

Referring again to FIG. 17, the dynamic portion of the head impulse test will be explained in detail. Initially, in step 528 of FIG. 17, when the subject's head 430 is displaced at or above a predetermined minimum velocity or speed (e.g., at or above 100 degrees per second) as measured by the motion sensing device 428, one or more configurations of the optotype 410 having a third size are displayed in succession on the output screen of the visual display device 404. In one or more embodiments, the optotype of step 528 has a third size that is greater than the size of the threshold version of the optotype determined in step 510. In these embodiments, the size of the threshold version of the optotype determined in step 510 may be multiplied by a scale factor (e.g., 1.5 or 1.75) to arrive at the third size (i.e., the increased size) of the optotype to be used in step 528. For example, in one or more embodiments, an optotype size that is two lines above the optotype size determined in step 510 on a Tumbling E eye chart may be used for the head impulse test. In other words, in one or more embodiments, the optotype size during the performance of the dynamic portion of the head impulse test is determined by increasing the optotype size determined in conjunction with the first set of successive trials by two sizes (e.g., by adding 0.2 logMAR to the static visual acuity determined during the first set of successive trials). During step 528, different configurations of the tumbling E optotype having the third size may be displayed one-at-time on the output screen of the visual display device 404. In the illustrative embodiment, the subject's head 430 may be displaced by the clinician 414 abruptly rotating the subject's to the right, or to the left, about the yaw axis 466 of FIG. 15 (i.e., approximately in a horizontal plane). For example, during one trial, the clinician 414 may rotate the subject's head 430 to the right about the yaw axis 466 between −20 degrees and 20 degrees (i.e., between 20 degrees to the left and 20 degrees to the right). Then, in the next trial, the clinician 414 may rotate the subject's head 430 to the left about the yaw axis 466 between 20 degrees and −20 degrees (i.e., between 20 degrees to the right and 20 degrees to the left). However, during the trials of the head impulse test, it is to be understood that the clinician 414 may randomly vary the rotation of the subject's head 430 between right and left rotations (i.e., the clinician 414 does not always alternate between right and left rotation, but rather may successively rotate in the same direction during consecutive trials). In the illustrative embodiment, the optotype 410 is displayed on the output screen of the visual display device 404 when the angular velocity of the head 430 of the subject 418 meets or exceeds a predetermined minimum angular velocity. For example, an exemplary head angular velocity curve 620, 626 generated during the performance of a head impulse test is illustrated in the graph 614 of FIG. 21. As shown in this figure, the y-axis 616 of the graph 614 is the head angular velocity in degrees per second, while the x-axis 618 of the graph 614 is the time in milliseconds (msec). In the graph 614 of FIG. 21, it can be seen that the head angular velocity curve 620, 626 has a first portion 620 where the head of the subject 418 is being rotated in a first direction (e.g., to the right) and a second portion 626 where the head of the subject 418 is being rotated in a second direction (e.g., to the left). In the first portion 620 of the head angular velocity curve 620, 626 for head rotation to the right, the computing device 402 initially determines when the head angular velocity reaches a first value 622. Once the computing device 402 has determined that the head angular velocity has reached the first value 622, the computing device 402 concludes that head 430 of the subject 418 is undergoing a head impulse displacement. The initial determination that the first threshold value 622 has been reached enables the computing device 402 to differentiate between mere noise in the head angular velocity signal measured the inertial measurement unit 428, and the actual occurrence of a head impulse displacement. Upon determining that the first threshold value 622 has been reached, the computing device 402 next determines when the head angular velocity reaches a second value 624 in the first portion 620 of the head angular velocity curve 620, 626 (i.e., the second value 624 is the minimum angular velocity for optotype display). Once the computing device 402 has determined that the head angular velocity has reached the second value 624, the computing device 402 displays the optotype 410 on the output screen of the visual display device 404. Referring again to FIG. 21, it can be seen that these same two threshold values 628, 630 are determined by the computing device 402 for the left head rotation in the second portion 626 of the head angular velocity curve 620, 626.

Also, during the dynamic portion of the head impulse test, the computing device 402 may be specially programmed to randomly choose the orientation of the optotype that is displayed on the screen. After the optotype disappears during the dynamic portion of the head impulse test, the subject 418 enters an optotype orientation response (i.e., the perceived configuration of the visual object 410) into the user input device 424, which transmits the response to the laptop computing device 402.

Figure 15:
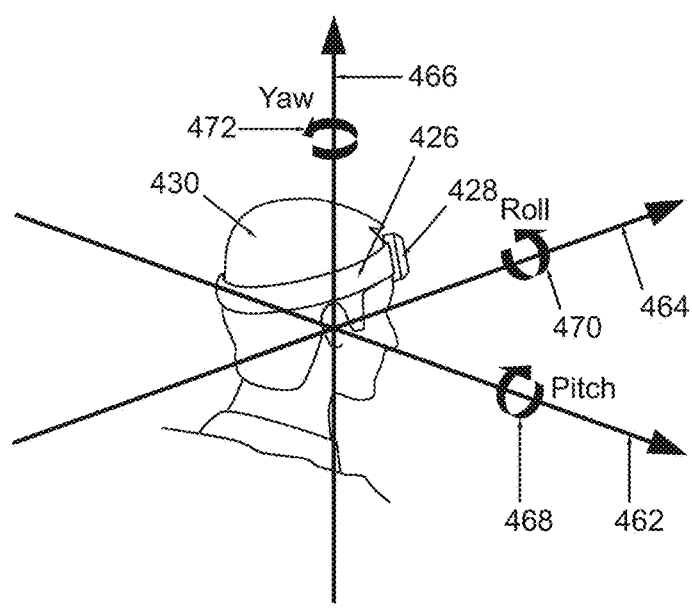
FIG. 15 is a diagrammatic view of the directions of subject head rotation that are capable of being measured with the motion sensing device of the vision testing systems described herein.

In alternative exemplary embodiments, rather than rotating the head 430 of the subject 418 about the yaw axis 466 in FIG. 15, the clinician 414 may alternatively rotate the head 430 of the subject 418 about the pitch axis 462 (i.e., approximately in a vertical plane) or about the roll axis 464 (i.e., in a roll plane). The computing device 402 is specially programmed to allow the clinician 414 to selectively choose any one of these rotational directions when performing the dynamic portion of the head impulse test.

Referring again to the flowchart of FIG. 17, the computing device or data processing device 402 determines whether or not the subject 418 correctly identifies one or more configurations (e.g., 410*a*, 410*b*, 410*c*, 410*d*) of the visual object 410 having the third size in step 530. For example, the subject 418 may be presented with one or more optotypes having the third size (e.g., a single optotype 410*a* pointing up). In the illustrative embodiment, during the dynamic set of trials performed during the head impulse test, each of the optotypes has the same physical size (i.e., each optotype has the same increased third size that is determined based upon the threshold size computed for the first series of trials carried out in steps 500-510 above). After each optotype in the trial is displayed to the subject 418, the subject 418 may utilize the user input device 424 (e.g., a wireless mouse) in order to transmit his or her response to the computing device 402 (e.g., the wireless mouse may have four buttons, each of which corresponds to one of the four configurations of the optotype). After receiving each of the subject's responses, the computing device 402 is specially programmed to determine if the subject 418 correctly determined the configuration of the optotype that was displayed on the output screen of the visual display device 404. For example, if the optotype 410*a* of FIG. 14 was displayed on the screen, the subject 418 must indicate that the optotype is pointing up to get the identification correct. Any other answer would be incorrect for this configuration of the optotype. Once the subject's answer or response is evaluated as to its correctness, the computing device 402 is specially programmed to record whether or not the subject 418 identified the optotype correctly.

In this manner, as set forth in step 532 of FIG. 17, the computing device 402 is specially programmed to determine whether or not the subject 418 correctly identified the configuration of the optotype 410 during a third set of successive trials (i.e., during the dynamic set of trials of the head impulse test). During the third set of successive trials, the angular velocity or speed of the head 430 of the subject 418 is measured by the motion sensing device 428 as the clinician 414 abruptly rotates the subject's to the right, or to the left, about the yaw axis 466 of FIG. 15 during a predetermined maximum number of trials (e.g., during fourteen (14) trials).

In step 534 of FIG. 18, after the subject 418 has completed a predetermined number of trials of optotype identification (e.g., fourteen (14) total trials), the computing device 402 is specifically programmed to determine the total number of visual object configurations (e.g., optotype configurations) that the subject 418 has identified correctly during the dynamic portion of the head impulse test (i.e., during the third set of successive trials). As an example, after the subject 418 completes one such series of trials of optotype identification, the computing device 402 may determine that the subject correctly identified nine (9) out of fourteen (14) optotype configurations correctly.

Next, in step 536 of FIG. 18, the computing device 402 is specifically programmed to generate a quantitative assessment of the head impulse test based upon the total number of visual object configurations (e.g., optotype configurations) that the subject 418 identified correctly during the dynamic portion of the head impulse test (i.e., during the third set of successive trials). Then, in step 538 of FIG. 18, the computing device 402 is specifically programmed to output the quantitative assessment of the head impulse test for the subject 418 on the output screen of the visual display device 404. The head impulse testing procedure concludes at step 540 in FIG. 18.

In one or more embodiments, the head impulse test may comprise a plurality of different sets of successive trials performed at different head velocities. For example, the first set of successive trials may be performed using a predetermined minimum velocity or speed of approximately 100 degrees per second (or 100 degrees per second), the second set of successive trials may be performed using a predetermined minimum velocity or speed of approximately 150 degrees per second (or 150 degrees per second), and the third set of successive trials may be performed using a predetermined minimum velocity or speed of approximately 200 degrees per second (or 200 degrees per second). In these one or more embodiments, different sets of successive trials may be performed at incrementally higher velocities or speeds over the course of the head impulse test.

In one or more embodiments, a baseline visual processing time and static visual acuity value must have been previously stored in the computing device 402 in order to permit the subject 418 to perform the dynamic portion of the head impulse test. For example, if no baseline visual processing time and static visual acuity was previously determined on the day of the head impulse test, the subject 418 must first complete the static visual acuity testing and the visual processing time testing prior to performing the dynamic portion of the head impulse test.

As briefly mentioned above, the stimulus levels and threshold determinations during the first and second sets of successive trials of the vision testing may be determined by the computing device 402 by means of executing a parameter estimation algorithm. In particular, during the first static set of successive trials during the head impulse test, the optotype size selected for each trial, and the threshold optotype size computed in step 510, may be computed using the parameter estimation algorithm. Similarly, during the visual processing time test performed in conjunction with the head impulse test, the optotype display time selected for each trial, and the threshold visual processing time computed in step 522, may be computed using the parameter estimation algorithm. As such, the parameter estimation computations performed by the computing device 402 will be explained in detail hereinafter.

Initially, the parameter estimation computational procedure during the first static set of successive trials during the head impulse test will be explained. In an exemplary embodiment, the optotype range for the set of static successive trials (i.e., static visual acuity (SVA) range) may be −0.3 logMAR to 1.0 logMAR, and it may be divided into steps of 0.05 logMAR, thereby resulting in a total of twenty-seven (27) steps overall. The initial optotype size that is presented to the subject by the computing device 402 is 0.4 logMAR. The initial optotype size of 0.4 logMAR is presumed to be easy for most subjects to recognize so that the configuration thereof will be properly identified. If the subject incorrectly identifies the configuration of the initial optotype, the computing device 402 increases the optotype size by four (4) steps so that the next optotype size presented to the subject is 0.6 logMAR. After every incorrect answer, the computing device 402 increases the optotype size by four (4) steps until the upper range limit of 1.0 logMAR is reached. The subject may be given one or more chances to answer correctly at the upper range limit of 1.0 logMAR. If the subject fails to correctly identify the configuration of the optotype with a size of 1.0 logMAR after having been given one or more chances, the computing device 402 will end the static portion of the test.

Conversely, if the subject correctly identifies the configuration of the initial optotype, the computing device 402 decreases the optotype size by three (3) steps so that the next optotype size presented to the subject is 0.25 logMAR. After every correct answer, the computing device 402 decreases the optotype size by three (3) steps until the subject identifies the optotype configuration incorrectly. At this point, the computing device 402 presumes that the subject's threshold must lie somewhere between the optotype sizes identified correctly and incorrectly. The process is continued, and the computing device 402 increases the optotype size by two (2) steps (0.1 logMAR) for every incorrect answer, and decreases the optotype size by one (1) step (0.05 logMAR) for every correct answer. Each time the subject correctly identifies the optotype configuration, the computing device 402 checks the number of correct answers and the number of incorrect answers for that particular threshold. When the computing device 402 determines that the percent ratio of correct answers to the total number of answers (correct/(correct+incorrect)*100) is between 50% and 75%, then the computing device 402 determines that the present optotype size is the subject's threshold. The computing device 402 further compares the number of correct and incorrect answers between the current optotype size and the next smaller optotype size. If the computing device 402 determines that the ratio of correct answers to the total number of answers is between 50% and 66%, then the static series of trials is ended, and the mean of the two (2) adjacent points (i.e., optotype sizes) is taken as the threshold. The static series of trials is continued by the computing device 402 until one of the two (2) conditions described above is fulfilled. For example, the total number of static trials conducted by the computing device 402 may be thirty (30) overall trials.

Now, the manner in which the computing device 402 carries out the parameter estimation computational procedure for the threshold visual processing time determination will be explained. The computational procedure for threshold visual processing time of the subject uses a visual processing time range of 35 milliseconds to 70 milliseconds, and it is divided into steps of 5.0 milliseconds, thereby resulting in a total of eight (8) steps overall. For the threshold visual processing time of the subject, the computing device 402 does not begin with a large initial step size. Rather, if the subject identifies the configuration of the optotype incorrectly, the computing device 402 increases the visual processing time by two (2) steps (10.0 milliseconds), while if the subject identifies the configuration of the optotype correctly, the computing device 402 decreases the visual processing time by one (1) step (5.0 milliseconds). During the visual processing time computational procedure, the computing device 402 performs the same two conditional comparisons described above for the static trials (i.e., determining whether between 50% and 75%, and whether between 50% and 66%).

Figure 22:
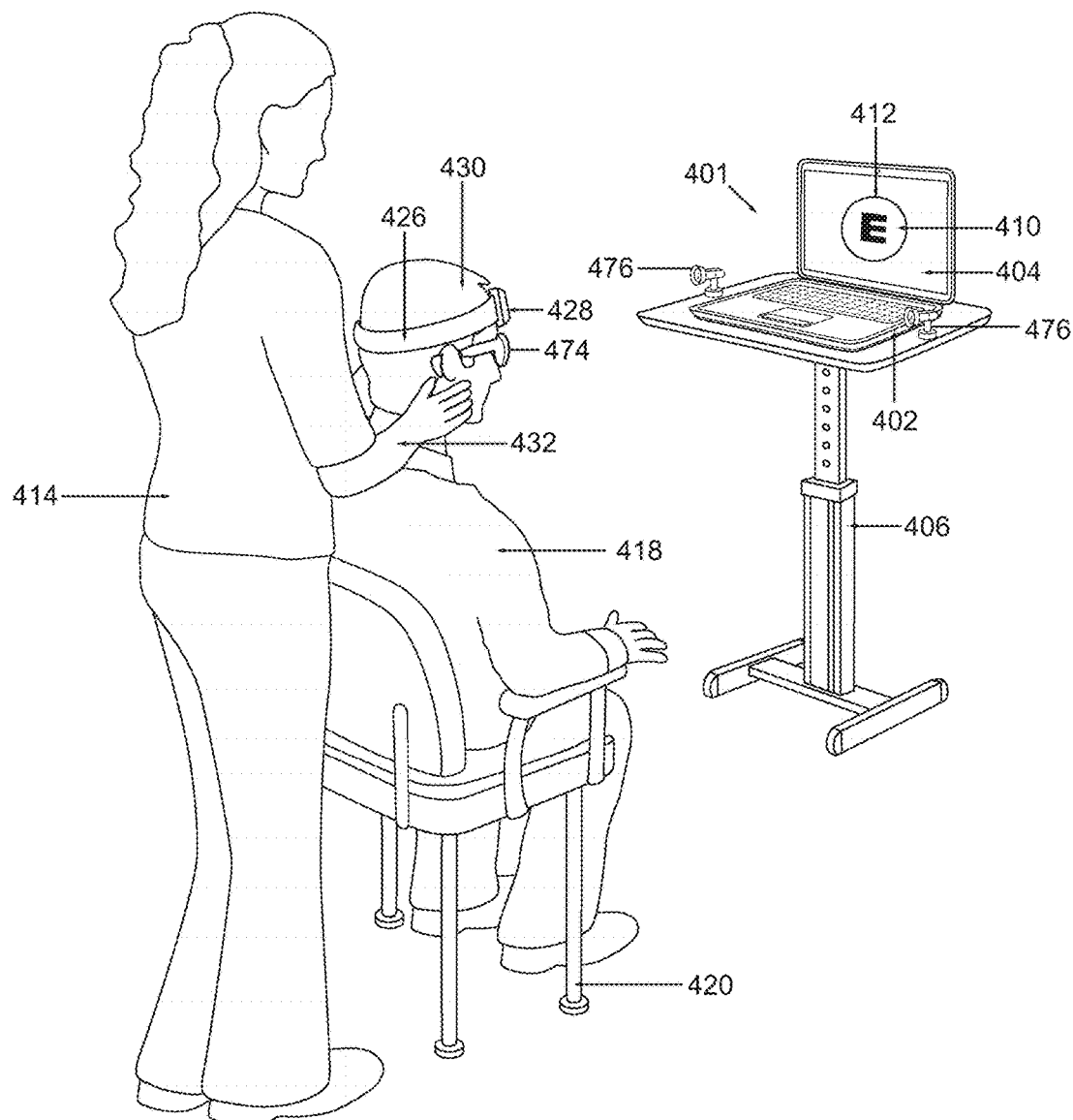
FIG. 22 is a diagrammatic perspective view of a second exemplary vision testing system with eye movement tracking, according to yet a further embodiment of the invention.

In accordance with a further illustrative embodiment of the invention, the subject may be outfitted with an eye movement tracking device 474 during the head impulse testing procedure so that the eye movement of the subject 418 may be tracked during the head impulse test (e.g., refer to FIG. 22). In particular, while the steps 528-532 in FIG. 17 are performed, the eye movement of the subject 418 may be continually tracked, and the eye position of the subject 418 may be correlated with subject's identification of the optotype to determine if there is a specific relationship between the position of the subject's eyes and whether or not the subject 418 correctly identifies the optotype.

Referring to FIG. 22, an exemplary embodiment of a system for testing the vision of a subject with eye movement tracking is seen generally at 401 in FIG. 22. The system 401 illustrated in FIG. 22 may be used for the head impulse testing procedure described above to determine if there a specific relationship between the position of the subject's eyes and whether or not the subject 418 correctly identifies the optotype. As shown in FIG. 22, the system 401 generally comprises a laptop computing device 402 (i.e., a computing device that is capable of collecting, storing, and processing data), which in turn, is operatively coupled to a head motion sensing device 428 and an eye movement tracking device 474. In FIG. 22, it can be seen that the eye movement tracking device 474 may be in the form of goggles or glasses worn on the head of the subject 418. The goggles or glasses worn on the head of the subject 418 may be in the form of one of the eye movement measurement devices 100, 200, which incorporate both video-based and infrared sensing means. In the illustrative embodiment, the eye movement measurement devices 100, 200 may be operatively connected to the laptop computing device 402 by means of either a wired connection or a wireless connection. In addition, the head motion sensing device 428 is removably coupled to the head 430 of the subject 418 using a stretchable, elastic headband 426 (i.e., a resilient band 426). In one or more alternative embodiments, the head motion sensing device may integrated into the goggles containing the eye movement tracking device 474 (e.g., the head motion sensing device 474 may be in the form of an inertial measurement unit (IMU) integrated in the goggles worn by the subject 418).

In one or more embodiments, the stretchable, elastic headband 426 that attaches the head motion sensing device 428 to the head 430 of the subject 418 may include a strap and a compressible piece of material disposed on an interior surface of the strap. When the head motion sensing device 428 is attached to the head 430 of the subject 418 by the headband 426, the compressible piece of material is configured to be disposed between a portion of the strap and the head 430 of the subject 418 so as to provide a cushion effect for the subject 418 (i.e., to improve the comfort of the subject 418 while wearing the device 428). In an exemplary embodiment, the compressible piece of material disposed on the interior surface of the strap may comprise a piece of foam, a polymeric material, such as silicone, or a composite material comprising a gel.

Figure 23:
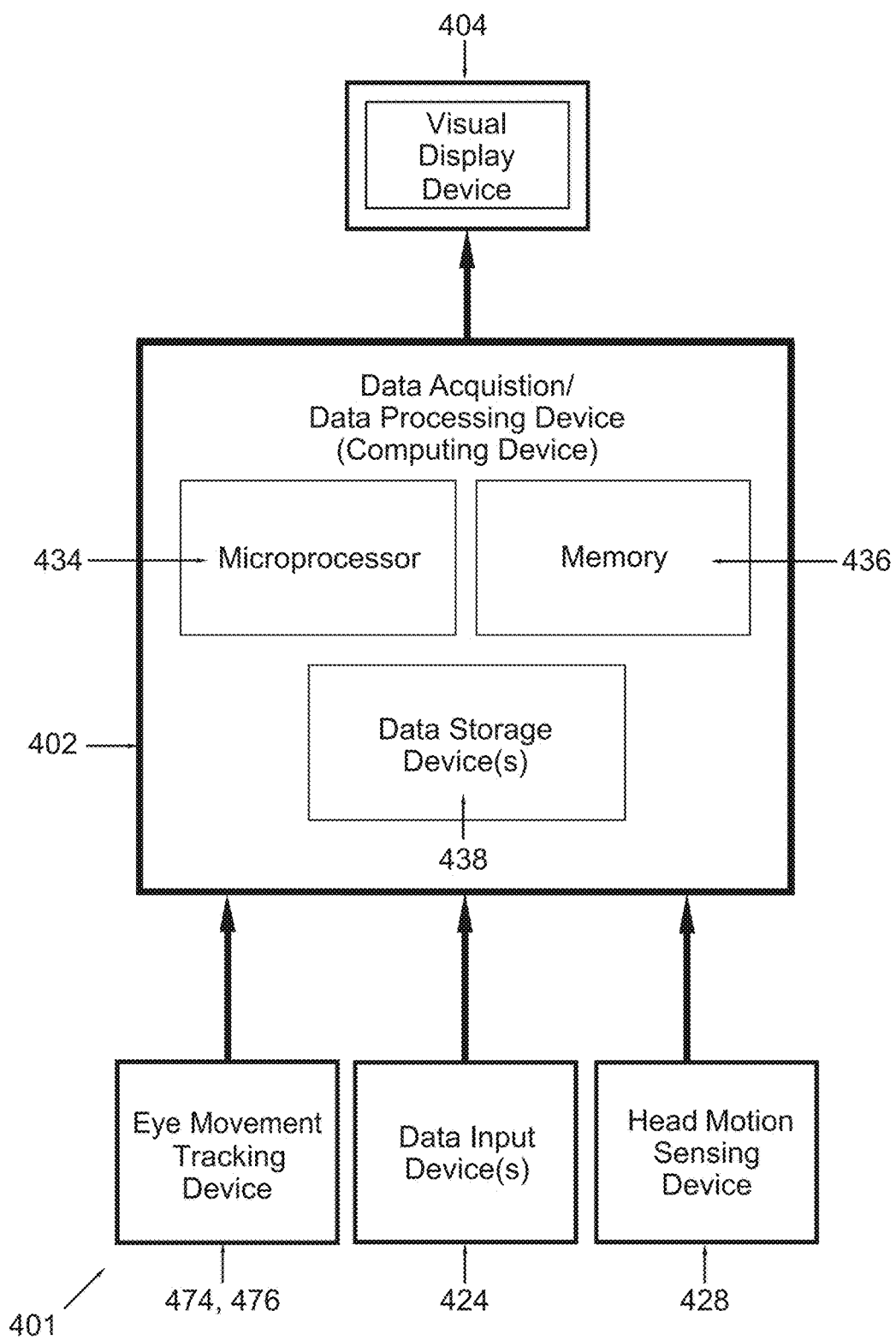
FIG. 23 is a block diagram of constituent components that may be utilized in the vision testing system with eye movement tracking of FIG. 22.

Now, turning to FIG. 23, it can be seen that the computing device 402 of the vision testing system with eye movement tracking 401 may comprise a microprocessor 434 for processing data, memory 436 (e.g., random access memory or RAM) for storing data during the processing thereof, and data storage device(s) 438, such as one or more hard drives, compact disk drives, floppy disk drives, flash drives, or any combination thereof. As shown in FIG. 23, the head motion sensing device 428, the eye movement tracking devices 474, 476, and the visual display device 404 are operatively coupled to the computing device 402 such that data is capable of being transferred between these devices. Also, as illustrated in FIG. 23, one or more data input devices, such as the wireless mouse 424, a keyboard, and a touchpad, are operatively coupled to the computing device 402 so that a user is able to enter data into the computing device 402. In some embodiments, the computing device 402 may be in the form of a laptop computer (as shown in FIG. 22), while in other embodiments, the computing device 402 may be embodied as a desktop computer.

In an alternative embodiment, rather than the eye movement tracking device 474 being integrated into goggles or glasses worn on the head of the subject 418, the eye movement tracking device may be in the form of one or more remote eye movement tracking devices 476 (e.g., in the form of eye movement tracking devices 476 disposed on the top surface of table 406). In this alternative embodiment, the eye movement tracking devices 476 (e.g., video-based and infrared sensing means) may capture the movement and/or position of the subject's eyes while he or she performs the head impulse testing procedure described above. As shown in FIG. 22, the eye movement tracking devices 476 may be in the form of video-based and infrared sensing means placed in front of the subject or patient 418. In the illustrative embodiment of FIG. 22, each of the eye movement tracking devices 476 may be configured to track one of the eyes of the subject 418 (i.e., the left eye movement tracking device 476 tracks the center of the pupil for left eye of the subject 418, while the right eye movement tracking device 476 tracks the center of the pupil for right eye of the subject 418). In the illustrative embodiment, the eye movement tracking devices 476 may be operatively connected to the laptop computing device 402 by means of either a wired connection or a wireless connection. Also, if markers are placed on the head 430 of the subject 418 (e.g., on the forehead of the subject 418), the movement of the head 430 of the subject 418 may also be determined using the devices 476, in addition to the eye movement of the subject 418. In one or more further embodiments, the eye movement tracking device 474 described above, which is disposed in the goggles or glasses worn by the subject 418, may be used in conjunction with the eye movement tracking devices 476 so as to form a hybrid system for tracking the eye movement of the subject 418.

Because the eye position of the subject 418 measured by the eye movement tracking devices 474, 476 is indicative of whether or not the subject 418 is able to see the visual object (i.e., the optotype) or not, in some further embodiments, the determination of the eye position for the subject 418 enables the head impulse testing procedure to be performed without requiring the subject 418 to identify the optotype (i.e., upon the determination by the computing device 402 that there is a specific relationship between the position of the subject's eyes and whether or not the subject 418 correctly identifies the optotype). For example, if the gaze direction of the subject's eyes, as determined using the eye movement tracking devices 474, 476, is not in the direction of the visual object (i.e., the optotype), the computing device 402 may determine that the subject 418 will not be able to identify the configuration of the optotype correctly. Conversely, if the gaze direction of the subject's eyes, as determined using the eye movement tracking devices 474, 476, is consistent with the location of the visual object (i.e., the optotype), the computing device 402 may determine that the subject 418 will be able to identify the configuration of the optotype correctly. However, in the other embodiments of the invention, it is preferred to have the subject 418 identify the optotype during the head impulse test while his or her eye movement is simultaneously measured.

It is apparent from the above detailed description that the vision testing systems 400, 401 and the methods performed thereby significantly advance the field of vision and vestibular assessment. For example, the vision testing systems 400, 401 described herein implement a customizable and accurate test for testing the vestibulo-ocular reflex (VOR) of a subject. In addition, the method described herein accurately tests the vestibulo-ocular reflex (VOR) of a subject by utilizing a test that is customized for the particular subject being tested.

While reference is made throughout this disclosure to, for example, "one embodiment" or a "further embodiment", it is to be understood that some or all aspects of these various embodiments may be combined with one another as part of an overall embodiment of the invention. That is, any of the features or attributes of the aforedescribed embodiments may be used in combination with any of the other features and attributes of the aforedescribed embodiments as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A system for testing the vision of a subject, said system comprising:
a motion sensing device, the motion sensing device configured to measure a velocity of a head of a subject;
a visual display device having an output screen, the visual display device configured to display one or more visual objects on the output screen so that the one or more visual objects are visible to the subject; and
a data processing device, the data processing device operatively coupled to the motion sensing device and the visual display device, the data processing device being specially programmed to:
display one or more configurations of the one or more visual objects on the output screen of the visual display device during one or more trials of a head impulse test, the one or more configurations of the one or more visual objects being displayed after the subject's head achieves a head velocity that meets or exceeds a predetermined threshold velocity value while the subject's head undergoes an impulse displacement, the head velocity of the subject being measured by the motion sensing device, the one or more configurations of the one or more visual objects being displayed for a predetermined time period;
determine whether or not the subject correctly identifies the one or more configurations of the one or more visual objects during the one or more trials of the head impulse test;
generate a quantitative assessment of the subject's performance during the one or more trials of the head impulse test based upon the number of visual object configurations that the subject identified correctly during the one or more trials; and
output the quantitative assessment of the head impulse test for the subject on the output screen of the visual display device.

2. The system according to claim 1, wherein the one or more visual objects displayed on the output screen of the visual display device comprise one or more optotypes, the one or more optotypes comprising at least one of: (i) a Tumbling E, (ii) a Landolt C, (iii) different letters of a recognized alphabet, and (iv) any other identifiable symbol.

3. The system according to claim 1, further comprising a user input device, the user input device configured to output an input signal in response to a manipulation of the user input device by a system user, the user input device being operatively coupled to the data processing device, the user input device configured to receive a response of the subject regarding the configuration of the one or more visual objects displayed on the output screen of the visual display device.

4. The system according to claim 3, wherein the user input device is configured to accept at least four different responses of a subject, each of the at least four different responses of the subject corresponding to a different configuration of the one or more visual objects.

5. The system according to claim 1, wherein the predetermined time period during which the one or more configurations of the one or more visual objects are displayed is based upon a visual processing time determined for the subject, and wherein the data processing device is specially programmed to determine the visual processing time for the subject based upon a series of successive test trials during which a display time of the one or more visual objects is varied for the subject.

6. The system according to claim 1, further comprising an eye movement tracking device operatively coupled to the data processing device, the eye movement tracking device comprising at least one non-video-based sensor configured to detect high speed eye movements of the one or more eyes of the subject during the impulse displacement of the subject's head.

7. The system according to claim 6, wherein the data processing device is specially programmed to determine whether a correlation exists between the eye position of the subject and whether or not the subject correctly identifies the one or more configurations of the one or more visual objects.

8. The system according to claim 1, wherein the data processing device is specially programmed to determine whether the subject's head achieves a preliminary threshold value prior to determining whether the subject's head velocity meets or exceeds the predetermined threshold velocity value so as to differentiate between signal noise and an impulse displacement of the subject's head; and wherein, upon determining that the subject's head achieves the preliminary threshold value, the data processing device is specially programmed to further determine whether the subject's head velocity meets or exceeds the predetermined threshold velocity value.

9. The system according to claim 1, wherein the one or more configurations of the one or more visual objects on the output screen have a display size, the display size of the one or more visual objects being determined based upon the performance of a static visual acuity test performed prior to the subject's head undergoing the impulse displacements, the data processing device being further specially programmed to:
prior to the subject's head undergoes the impulse displacements, display one or more configurations of one or more visual objects having an initial size on the output screen of the visual display device while the subject maintains a generally fixed position of his or her head during the static visual acuity test;
determine whether or not the subject correctly identifies the one or more configurations of the one or more visual objects having the initial size;
incrementally decrease and/or increase the size of the one or more visual objects on the output screen of the visual display device during a static set of successive trials, and determine whether or not the subject correctly identifies one or more configurations of each of the differently sized visual objects during the static set of successive trials while the subject maintains a generally fixed position of his or her head;
determine a size parameter of a threshold version of the one or more visual objects based upon a performance of the subject during the static set of successive trials during which the subject maintains the generally fixed position of his or her head; and
set the display size of the one or more visual objects displayed while the subject's head undergoes the impulse displacements based upon the size parameter of the threshold version of the one or more visual objects.

10. The system according to claim 1, wherein the motion sensing device is in the form of an inertial measurement unit.

11. A method for testing the vision of a subject, said method comprising the steps of:
providing a motion sensing device, the motion sensing device configured to measure a velocity of a head of a subject;
providing a visual display device having an output screen, the visual display device configured to display one or more visual objects on the output screen so that the one or more visual objects are visible to the subject;
providing a data processing device, the data processing device operatively coupled to the the motion sensing device and the visual display device;
positioning the subject in front of the output screen of the visual display device such that one or more visual objects are visible to the subject;
displaying one or more configurations of the one or more visual objects on the output screen of the visual display device during one or more trials of a head impulse test, the one or more configurations of the one or more visual objects being displayed after the subject's head achieves a head velocity that meets or exceeds a predetermined threshold velocity value while the subject's head undergoes an impulse displacement, the head velocity of the subject being measured by the motion sensing device, the one or more configurations of the one or more visual objects being displayed for a predetermined time period;
determining, by using the data processing device, whether or not the subject correctly identifies the one or more configurations of the one or more visual objects during the one or more trials of the head impulse test;
generating, by using the data processing device, a quantitative assessment of the subject's performance during the one or more trials of the head impulse test based upon the number of visual object configurations that the subject identified correctly during the one or more trials; and
outputting the quantitative assessment of the head impulse test for the subject on the output screen of the visual display device.

12. The method according to claim 11, wherein the one or more visual objects displayed on the output screen of the visual display device comprise one or more optotypes, the one or more optotypes comprising at least one of: (i) a Tumbling E, (ii) a Landolt C, (iii) different letters of a recognized alphabet, and (iv) any other identifiable symbol.

13. The method according to claim 11, further comprising a user input device, the user input device configured to output an input signal in response to a manipulation of the user input device by a system user, the user input device being operatively coupled to the data processing device; and wherein the method further includes the step of:
inputting a response of the subject regarding the configuration of the one or more visual objects into the user input device, outputting an input signal from the user input device that is indicative of the response of the subject, and transmitting the input signal of the user input device to the data processing device so that the data processing device is capable of determining whether or not the subject has correctly identified a configuration of the one or more visual objects based upon the response of the subject.

14. The method according to claim 13, wherein the user input device is configured to accept at least four different responses of a subject, each of the at least four different responses of the subject corresponding to a different configuration of the one or more visual objects.

15. The method according to claim 11, wherein the predetermined time period during which the one or more configurations of the one or more visual objects are displayed is based upon a visual processing time determined for the subject; and wherein the method further includes the step of:
determining, by using the data processing device, the visual processing time for the subject based upon a series of successive test trials during which a display time of the one or more visual objects is varied for the subject.

16. The method according to claim 11, further comprising an eye movement tracking device operatively coupled to the data processing device, the eye movement tracking device comprising at least one non-video-based sensor configured to detect high speed eye movements of the one or more eyes of the subject during the impulse displacement of the subject's head; and wherein the method further includes the step of:
 measuring, by using the eye movement tracking device, an eye position of the subject while the subject's head undergoes the impulse displacement.

17. The method according to claim 16, wherein the method further includes the step of:
 determining, by using the data processing device, whether a correlation exists between the eye position of the subject and whether or not the subject correctly identifies the one or more configurations of the one or more visual objects.

18. The method according to claim 11, wherein the method further includes the steps of:
 determining, by using the data processing device, whether the subject's head achieves a preliminary threshold value prior to determining whether the subject's head velocity meets or exceeds the predetermined threshold velocity value so as to differentiate between signal noise and an impulse displacement of the subject's head; and
 upon determining that the subject's head achieves the preliminary threshold value, further determining, by using the data processing device, whether the subject's head velocity meets or exceeds the predetermined threshold velocity value.

19. The method according to claim 11, wherein the one or more configurations of the one or more visual objects on the output screen have a display size, the display size of the one or more visual objects being determined based upon the performance of a static visual acuity test performed prior to the subject's head undergoing the impulse displacements; and wherein the method further includes the steps of:
 prior to the subject's head undergoing the impulse displacements, displaying one or more configurations of one or more visual objects having an initial size on the output screen of the visual display device while the subject maintains a generally fixed position of his or her head during the static visual acuity test;
 determining, by using the data processing device, whether or not the subject correctly identifies the one or more configurations of the one or more visual objects having the initial size;
 incrementally decreasing and/or increasing the size of the one or more visual objects on the output screen of the visual display device using the data processing device during a static set of successive trials, and determining whether or not the subject correctly identifies one or more configurations of each of the differently sized visual objects during the static set of successive trials while the subject maintains a generally fixed position of his or her head;
 determining, by using the data processing device, a size parameter of a threshold version of the one or more visual objects based upon a performance of the subject during the static set of successive trials during which the subject maintains the generally fixed position of his or her head; and
 setting, by using the data processing device, the display size of the one or more visual objects displayed while the subject's head undergoes the impulse displacements based upon the size parameter of the threshold version of the one or more visual objects.

20. The method according to claim 11, wherein the motion sensing device is in the form of an inertial measurement unit.

* * * * *